(12) United States Patent
Young

(10) Patent No.: US 12,371,455 B2
(45) Date of Patent: Jul. 29, 2025

(54) SAPOVIRUS VACCINES

(71) Applicant: VST LLC, Brookings, SD (US)

(72) Inventor: Alan John Young, Brookings, SD (US)

(73) Assignee: VST LLC, Brookings, SD (US)

( * ) Notice: Subject to any disclaimer, the term of this patent is extended or adjusted under 35 U.S.C. 154(b) by 654 days.

(21) Appl. No.: 17/851,492

(22) Filed: Jun. 28, 2022

(65) Prior Publication Data

US 2023/0015570 A1 Jan. 19, 2023

Related U.S. Application Data

(60) Provisional application No. 63/215,571, filed on Jun. 28, 2021.

(51) Int. Cl.
*C07K 14/005* (2006.01)
*A61K 39/12* (2006.01)
*A61P 31/14* (2006.01)
*A61K 39/00* (2006.01)

(52) U.S. Cl.
CPC ............ *C07K 14/005* (2013.01); *A61K 39/12* (2013.01); *A61P 31/14* (2018.01); *A61K 2039/54* (2013.01); *A61K 2039/541* (2013.01); *A61K 2039/545* (2013.01); *C12N 2770/16022* (2013.01); *C12N 2770/16034* (2013.01); *C12N 2770/16051* (2013.01); *C12N 2770/16071* (2013.01)

(58) Field of Classification Search
None
See application file for complete search history.

(56) References Cited

U.S. PATENT DOCUMENTS

2014/0004145 A1* 1/2014 Taylor .................... A61P 31/12
530/416

OTHER PUBLICATIONS

Wang et al., Transbound Emerg Dis. 2020, 67:18-28 (Year: 2020).*
Shen et al., Transbound Emerg Dis., 2022, 69:1246-1255 (Year: 2022).*
Shen et al., Transbound Emerg Dis., 2022, 69:1246-1255, website printout from https://pubmed.ncbi.nlm.nih.gov/33780163/, accessed May 7, 2025, showing publication date of Mar. 29, 2021, 26 pages (Year: 2022).*
GenBank Accession No. QHC33961 Porcine Sapovirus strain NE7. 5, 2020 (Year: 2020).*
GenBank Accession No. QHC33969 Porcine Sapovirus strain KS8. 7A, 2020 (Year: 2020).*
GenBank Accession No. QHC33967 Porcine Sapovirus strain MO13472, 2020 (Year: 2020).*
GenBank Accession No. MW316754 Porcine Sapovirus strain SaV/GIII/USA/NE_7211-3/2019 (Year: 2021).*
GenBank Accession No. QHC33965 Porcine Sapovirus strain NE9550, 2020 (Year: 2020).*

* cited by examiner

*Primary Examiner* — Stacy B Chen

(57) ABSTRACT

The present invention describes immunogenic compositions containing immunogenic polypeptides of Sapovirus, including immunogenic compositions containing antigens other than Sapovirus antigens, including antigens that may be used in immunization against pathogens that cause diarrheal diseases. Methods of eliciting an immune response with the immunogenic compositions as disclosed and methods of treating a Sapovirus infection are also described.

18 Claims, 2 Drawing Sheets

Specification includes a Sequence Listing.

SAPOVIRUS VACCINES

CROSS REFERENCE TO RELATED APPLICATION

This application claims benefit under 35 U.S.C. § 119(e) to U.S. Provisional Application No. 63/215,571, filed Jun. 28, 2021, which is incorporated by reference herein in its entirety.

FIELD OF INVENTION

The present invention pertains generally to compositions that elicit immune responses against Sapoviruses. In particular, the invention relates to immunogenic compositions (e.g., vaccines) comprising immunogenic polypeptides of Sapovirus. Immunogenic compositions, in addition, may contain antigens other than Sapovirus antigens. Methods of eliciting an immune response with the immunogenic compositions as disclosed herein and methods of treating a Sapovirus infection are also described.

BACKGROUND INFORMATION

Sapoviruses (also known as Sapporo-like viruses) are etiological agents of acute gastroenteritis. Sapoviruses are members of the Caliciviridae family of small, nonenveloped viruses, 27-35 nm in diameter, containing a single-strand of positive-sense genomic RNA.

Natural hosts for the virus are humans and swine. The virus is transmitted through oral/fecal contact. Symptoms most commonly include diarrhea and vomiting. The Sapovirus was initially discovered in an outbreak of gastroenteritis in an orphanage in Sapporo, Japan, 1977.

After an incubation period of 1-4 days, signs of illness start to arise. Symptoms of Sapovirus are very similar to those of norovirus. The most common symptoms are vomiting and diarrhea; however, additional symptoms may occur-fever is very rare. While individuals most frequently start to show symptoms after the 1-4 day incubation period, there have been cases in which an individual is asymptomatic. Although the individual does not show symptoms, they are still capable of spreading the virus through the general mode of transmission, the oral-fecal route.

There remains a need for an improved therapy for treating subjects having gastroenteritis associated with Sapovirus infection and methods for preventing the spread of infection.

SUMMARY OF THE INVENTION

The present invention provides immunogenic compositions comprising Sapovirus antigens, in particular as a part of subunit vaccines.

In embodiments, methods for producing Sapovirus-derived immunogenic polypeptides and/or peptides may be mixed or co-expressed with adjuvants are disclosed. Immunogenic compositions may include one or more polypeptides and/or adjuvants as described herein. For example, immunogenic compositions may comprise other antigens that may be used in immunization against pathogens that cause diarrheal diseases, such as antigens derived from rotavirus.

In embodiments, a process for producing a polypeptide is disclosed including the step of culturing a host cell transformed with a nucleic acid as described herein under conditions which induce polypeptide expression. In a related aspect, a Sapovirus protein may be expressed by recombinant technology and used to develop an immunogenic composition comprising a recombinant antigenic subunit, where such expressed polypeptide is generated using baculovirus/insect cell methodology.

In one aspect, a process for producing nucleic acid is disclosed, where the nucleic acid encoding a Sapovirus derived protein or polypeptide is prepared (at least in part) by chemical synthesis. In a related aspect, the process includes amplifying nucleic acids using a primer-based amplification method (e.g., PCR). In a related aspect, the primers for such reactions include, but are not limited to, SEQ ID NOs: 3, 4, 5, 6, 9, 10, 11, 12, 13, 22, 23, 24, 25, and combinations thereof.

In another aspect, a process for producing a protein complex is disclosed, including administering a Sapovirus derived polypeptide, or a fragment thereof, to a subject. In a related aspect, the process includes admixing a Sapovirus-derived polypeptide with a pharmaceutically acceptable carrier or diluent. In a further related aspect, the composition may include the polypeptide as set forth in SEQ ID NO:2, SEQ ID NO:8, SEQ ID NO:15, SEQ ID NO:21 or a combination thereof. In a still further related aspect, the Sapovirus polypeptide comprises VP1. In another aspect, the composition may contain more than one Sapovirus VP1, wherein the more than one VP1s are from more than one strain.

In embodiments, a method of eliciting an immunological response in a subject is disclosed including administering a composition of the instant disclosure. In a related aspect, the method further includes administering an adjuvant. In a further related aspect, the method includes administering the immunogenic composition to the subject via topical, parenteral or mucosal route.

In one aspect, the administration may be multiple administrations, where a first immunogenic composition and a second immunogenic composition are the same. In another aspect, the first immunogenic composition and the second immunogenic composition are different.

In one aspect, administration is performed two or more times.

In embodiments, a medicament for use in treating an infection by a Sapovirus in a subject in need thereof comprising a therapeutically effective amount of an immunogenic composition above is disclosed.

In embodiments, a method for treating an infection by a Sapovirus is disclosed including administering to a subject in need thereof a therapeutically effective amount of an immunogenic composition as described herein.

In a related aspect, the method includes mucosally administering a therapeutically effective amount of a first immunogenic composition comprising one or more Sapovirus antigens and topically or parenterally administering a therapeutically effective amount of a second immunogenic composition comprising one or more Sapovirus antigens.

In one aspect, multiple therapeutically effective doses of the immunogenic composition are administered to a subject. In another aspect, an immunogenic composition comprises a rotavirus antigen.

In embodiments, an isolated recombinant nucleic acid encoding a Sapovirus VP1 protein is disclosed, where the encoding nucleic acid includes i) a sequence including SEQ ID NO:1, SEQ ID NO:7, SEQ ID NO:14, SEQ ID NO:20, and combinations thereof or ii) nucleic acid having at least 80% sequence identity to the nucleic acid sequences as set forth in SEQ ID NO:1, SEQ ID NO:7, SEQ ID NO:14, SEQ ID NO:20 or combinations thereof.

In one aspect, the encoding nucleic acid is recombined with a vector. In a related aspect, the vector is a baculovirus vector. In another related aspect, the vector is contained in a host cell. In a further related aspect, the host cell is an insect cell.

These and other embodiments of the instant subject matter as disclosed will readily occur to those of skill in the art in view of the instant disclosure.

Figure 1:
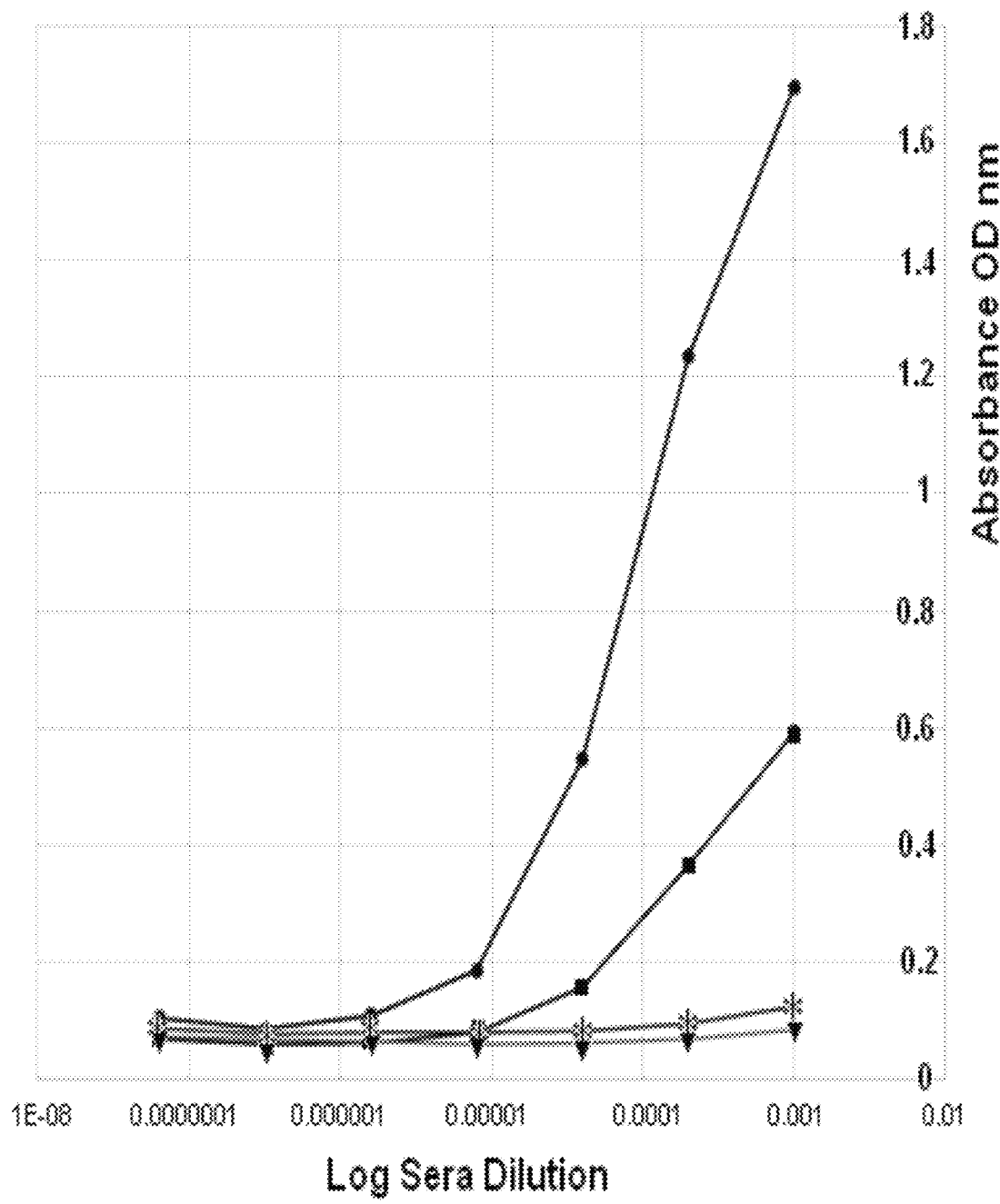
FIG. 1 is a graph showing a comparison of Homologous vs Heterologous Coating Antigen, x access=Sera Dilution, Y access=Optical Density. (-●- V19030-060920 Sapovirus Pool Avg OD; -■- IAV-S H3 Vaccinate Pool Avg OD; - * - V19030-060920 Sapovirus Non-Vaccinated Control Pool Avg OD V19045-120321A; -▼- IAV-S H3 Non-Vaccinated Control Pool Avg OD).

FIG. 2 is a graph showing a serological assessment of vaccinates vs non-vaccinates via ELISA (same axis as noted in FIG. 1)(-●- 860 Vaccinate; -■- 861 Vaccinate; - * - 862 Vaccinate; -▼- 863 Vaccinate; -▲- 864 Vaccinate; -◀ -865 Vaccinate; -°- 866 Vaccinate; -◆-867 Non-Vacc; -▶ - 868 Non-Vacc; -x- 869 Non-Vacc).

DETAILED DESCRIPTION OF THE INVENTION

Before the present composition, methods, and methodologies are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Any methods and materials similar or equivalent to those described herein may be used in the practice or testing of the invention, as it will be understood that modifications and variations are encompassed within the spirit and scope of the instant disclosure.

As used herein, "about," "approximately," "substantially" and "significantly" will be understood by a person of ordinary skill in the art and will vary in some extent depending on the context in which they are used. If there are uses of the term which are not clear to persons of ordinary skill in the art given the context in which it is used, "about" and "approximately" will mean plus or minus<10% of particular term and "substantially" and "significantly" will mean plus or minus>10% of the particular term. In embodiments, compositions may "contain," "comprise" or "consist essentially of" a particular component or group of components, where the skilled artisan would understand the latter to mean the scope of the claim is limited to the specified materials or steps "and those that do not materially affect the basic and novel characteristic(s)" of the claimed invention.

As used herein, the terms "Sapovirus" and "Sapporo-like virus" refer to members of the genus Sapovirus of the family Caliciviridae of positive-sense, single-stranded RNA, non-enveloped viruses. The term Sapovirus includes strains in all genogroups of the virus. Currently, Sapovirus strains are divided into five genogroups (GI-GV) based on their capsid (VP1) sequences. The term Sapovirus may include, but is not limited to, the species Sapporo virus, London/29845 virus, Manchester virus, Houston/86 virus, Houston/90 virus, and Parkville virus. A large number of Sapovirus isolates have been partially or completely sequenced. The term Sapovirus also includes isolates not characterized at the time of filing.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include post-expression modifications of the polypeptide, for example, glycosylation, acetylation, phosphorylation and the like. Furthermore, for purposes of the present disclosure, a "polypeptide" refers to a protein which includes modifications, such as deletions, additions and substitutions (generally conservative in nature), to the native sequence, so long as the protein maintains the desired activity. These modifications may be deliberate, as through site-directed mutagenesis, or may be accidental, such as through mutations of hosts which produce the proteins or errors due to PCR amplification.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises about 50%, about 80%-85%, or about 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism or cell with which the molecule is found in nature or is present in the substantial absence of other biological macro-molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used include fluorescein, rhodamine, dansyl, umbelliferone, Texas red, luminol, acradimum esters, NADPH and α-β-galactosidase.

"Homology" refers to the percent identity between two polynucleotide or two polypeptide moieties. Two nucleic acid, or two polypeptide sequences are "substantially homologous" to each other when the sequences exhibit at least about 50% sequence identity, at least about 75% sequence identity, at least about 80%-85% sequence identity, at least about 90% sequence identity, and at least about 95%-98% sequence identity over a defined length of the molecules. As used herein, substantially homologous also refers to sequences showing complete identity to the specified sequence. In one aspect, antigens as disclosed herein may exclude naturally occurring Sapovirus sequences (i.e., amino acid sequences having 100% homology to the naturally occurring Sapovirus VP1 amino acid sequence or naturally occurring nucleic acid sequence encoding said amino acid sequence).

In general, "identity" refers to an exact nucleotide-to-nucleotide or amino acid-to-amino acid correspondence of two polynucleotides or polypeptide sequences, respectively. Percent identity may be determined by a direct comparison of the sequence information between two molecules by aligning the sequences, counting the exact number of matches between the two aligned sequences, dividing by the length of the shorter sequence, and multiplying the result by 100. Readily available computer programs may be used to aid in the analysis, such as ALIGN, Dayhoff, M. O. in Atlas of Protein Sequence and Structure M. O. Dayhoff, ed., 5 Suppl. 3:353-358, National biomedical Research Foundation, Washington, D.C., which adapts the local homology algorithm of Smith and Waterman Advances in Appl. Math. 2:482-489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence may be determined using the homology algorithm of Smith and Waterman with a default scoring table and a gap penalty of six nucleotide positions.

Another method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, CA). From this suite of packages the Smith-Waterman algorithm may be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP may be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs are readily available. In one aspect, antigens as disclosed herein may exclude naturally occurring Sapovirus sequences (i.e., amino acid sequences having 100% identity to the naturally occurring Sapovirus VP1 amino acid sequence or naturally occurring nucleic acid sequence encoding said amino acid sequence).

Alternatively, homology may be determined by hybridization of polynucleotides under conditions which form stable duplexes between homologous regions, followed by digestion with single-stranded-specific nuclease(s), and size determination of the digested fragments. DNA sequences that are substantially homologous may be identified in a Southern hybridization experiment under, for example, stringent conditions, as defined for that particular system. Defining appropriate hybridization conditions is within the skill of the art.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which may be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence may be determined by a start codon at the 5' (amino) terminus and a translation stop codon at the 3' (carboxy) terminus. A coding sequence may include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

The term "nucleic acid" includes DNA and RNA, and also their analogues, such as those containing modified backbones (e.g., phosphorothioates, and the like), and also peptide nucleic acids (PNA), and the like. The present disclosure provides nucleic acids comprising sequences complementary to those described above (e.g., for antisense or probing purposes).

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences may be present between the promoter sequence and the coding sequence and the promoter sequence may still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, at least 8 to 10 amino acids, and at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. In embodiments, the expression cassette described herein may be contained within a plasmid construct. In addition to the components of the expression cassette, the plasmid construct may also include, one or more selectable markers, a signal which allows the plasmid construct to exist as single-stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, less than about 70%, and less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. Such techniques may be used to introduce one or more exogenous DNA moieties into suitable host cells. The term refers to both stable and transient uptake of the genetic material, and includes uptake of peptide- or antibody-linked DNAs.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which may transfer nucleic acid sequences to target cells. Thus, the term includes cloning and expression vehicles, as well as viral vectors.

By "fragment" is intended a molecule consisting of only a part of the intact full-length sequence and structure. A fragment of a polypeptide may include a C-terminal deletion, an N-terminal deletion, and/or an internal deletion of the native polypeptide. A fragment of a polypeptide will generally include at least about 5-10 contiguous amino acid residues of the full-length molecule, at least about 15-25 contiguous amino acid residues of the full-length molecule, and at least about 20-50 or more contiguous amino acid residues of the full-length molecule, or any integer between 5 amino acids and the number of amino acids in the full-length sequence, provided that the fragment in question retains the ability to elicit the desired biological response. A fragment of a nucleic acid may include a 5'-deletion, a 3-deletion, and/or an internal deletion of a nucleic acid. Nucleic acid fragments will generally include at least about 5-1000 contiguous nucleotide bases of the full-length molecule and may include at least 5, 10, 15, 20, 25, 30, 40, 50, 60, 75, 100, 150, 250 or at least 500 contiguous nucleotides of the full-length molecule, or any integer between 5 nucleotides and the number of nucleotides in the full-length sequence. Such fragments may be useful in hybridization, amplification, production of immunogenic fragments, or nucleic acid immunization.

By "immunogenic fragment" is meant a fragment of an immunogen which includes one or more epitopes and thus may modulate an immune response or may act as an adjuvant for a co-administered antigen. Such fragments may be identified using any number of epitope mapping techniques, well known in the art. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871, incorporated herein by reference in its entirety. Similarly, conformational epitopes are readily identified by determining spatial conformation of amino acids such as by, e.g., x-ray crystallography and 2-dimensional nuclear magnetic resonance.

Immunogenic fragments, for purposes of the present disclosure, will usually be at least about 2 amino acids in length, about 5 amino acids in length, and at least about 10 to about 15 amino acids in length. There is no critical upper limit to the length of the fragment, which could comprise nearly the full-length of the protein sequence, or even a fusion protein comprising two or more epitopes.

As used herein, the term "epitope" generally refers to the site on an antigen which is recognized by a T-cell receptor and/or an antibody. In embodiments, it is a short peptide derived from or as part of a protein antigen. However, the term is also intended to include peptides with glycopeptides and carbohydrate epitopes. Several different epitopes may be carried by a single antigenic molecule. The term "epitope" also includes modified sequences of amino acids or carbohydrates which stimulate responses which recognize the whole organism. It is advantageous if the selected epitope is an epitope of an infectious agent, which agent causes the infectious disease.

The epitope may be generated from knowledge of the amino acid and corresponding DNA sequences of the peptide or polypeptide, as well as from the nature of particular amino acids (e.g., size, charge, and the like) and the codon dictionary, without undue experimentation. Some guidelines in determining whether a protein will stimulate a response, include: Peptide length—the peptide is about 8 or 9 amino acids long to fit into the MHC class I complex and about 13-25 amino acids long to fit into a class II MHC complex. This length is a minimum for the peptide to bind to the MHC complex. In one aspect, the peptides may be longer than these lengths because cells may cut peptides. The peptide may contain an appropriate anchor motif which will enable it to bind to the various class I or class II molecules with high enough specificity to generate an immune response. This may be done, without undue experimentation, by comparing the sequence of the protein of interest with published structures of peptides associated with the MHC molecules. Thus, the skilled artisan may ascertain an epitope of interest by comparing the protein sequence with sequences listed in the protein database.

As used herein, the term "T cell epitope" refers generally to those features of a peptide structure which are capable of inducing a T cell response and a "B cell epitope" refers generally to those features of a peptide structure which are capable of inducing a B cell response.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes may be generated to allow for the future protection of an immunized host.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. Recent methods of measuring cell-mediated immune response include measurement of intracellular cytokines or cytokine secretion by T-cell populations, or by measurement of epitope specific T-cells.

Thus, an immunological response as used herein may be one that stimulates the production of antibodies (e.g., neutralizing antibodies that block bacterial toxins and pathogens such as viruses entering cells and replicating by binding to toxins and pathogens, typically protecting cells from infection and destruction). The antigen of interest may also elicit production of CTLs. Hence, an immunological response may include one or more of the following effects: the production of antibodies by B-cells; and/or the activation of suppressor T-cells and/or memory/effector T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses may be determined using standard immunoassays and neutralization assays, well known in the art. The innate immune system of mammals also recognizes and responds to molecular features of pathogenic organisms via activation of Toll-like receptors and similar receptor molecules on immune cells. Upon activation of the innate immune system, various non-adaptive immune response cells are activated to, e.g., produce various cytokines, lymphokines and chemokines. Cells activated by an innate immune response include immature and mature Dendritic cells of the monocyte and plamsacytoid lineage (MDC, PDC), as well as gamma, delta, alpha and beta T cells and B cells and the like. Thus, the present disclosure also contemplates an immune response wherein the immune response involves both an innate and adaptive response.

An "immunogenic composition" is a composition that comprises an antigenic molecule where administration of the composition to a subject results in the development in the subject of a humoral and/or a cellular immune response to the antigenic molecule of interest.

The terms "immunogenic" protein or polypeptide refer to an amino acid sequence which elicits an immunological response as described above. An "immunogenic" protein or polypeptide, as used herein, includes the full-length sequence of the protein in question, including the precursor and mature forms, analogs thereof, or immunogenic fragments thereof.

"Gene transfer" or "gene delivery" refers to methods or systems for reliably inserting DNA or RNA of interest into a host cell. Such methods may result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses. When used for immunization, such gene delivery expression vectors may be referred to as vaccines or vaccine vectors.

The term "derived from" is used herein to identify the original source of a molecule but is not meant to limit the method by which the molecule is made which may be, for example, by chemical synthesis or recombinant means.

Generally, a viral polypeptide is "derived from" a particular polypeptide of a virus (viral polypeptide) if it is (i) encoded by an open reading frame of a polynucleotide of that virus (viral polynucleotide), or (ii) displays sequence identity to polypeptides of that virus as described above.

A polynucleotide "derived from" a designated sequence refers to a polynucleotide sequence which comprises a contiguous sequence of approximately at least about 6 nucleotides, at least about 8 nucleotides, at least about 10-12 nucleotides, and at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

A Sapovirus polynucleotide, oligonucleotide, nucleic acid, protein, polypeptide, or peptide, as defined above, is a molecule derived from a Sapovirus, respectively, including, without limitation, any of the various isolates of Sapovirus. The molecule need not be physically derived from the particular isolate in question, but may be synthetically or recombinantly produced.

The genomes of Sapovirus strains contain either two or three open reading frames. In strains of Sapovirus having two open reading frames, ORF1 encodes a polyprotein comprising both nonstructural and structural proteins. The capsid protein VP1 is encoded by ORF1 as a component of the Sapovirus polyprotein, and the minor structural protein VP10 is encoded by ORF2. In strains of Sapovirus having three open reading frames, a stop codon precedes the coding region for the capsid protein. A polyprotein not including the capsid protein is encoded by ORF1, the capsid protein VP1 is encoded by ORF2, and the minor structural protein VP10 is encoded by ORF3.

Cleavage of the Sapovirus strain Mc10 polyprotein (GenBank Accession No. AY237420) by a 3C-like protease produces at least ten distinct products, p11, p28, p35 (NTPase), p32, p14 (VPg), p70 (Pro-Pol), p60 (VP1). The polyprotein comprises the polypeptides in the order of $NH_2$-p11-p28-NTPase-p32-VPg-p70(Pro-Pol)-VP1-COOH. The p70 (Pro-Pol) region of the polyprotein resides at residues 1056-1720, and the VP1 region of the polyprotein resides at residues 1721-2278. Although, the foregoing numbering is relative to the polyprotein amino acid sequence of Sapovirus strain Mc10, it is to be understood that the corresponding amino acid positions in sequences obtained from other genotypes and isolates of Sapovirus are also intended to be encompassed by the present disclosure. Any one of the polypeptides encoded by ORF1, or the full-length polyprotein, VP1, or VP10, as well as variants thereof, immunogenic fragments thereof, and nucleic acids encoding such polypeptides, variants or immunogenic fragments may be used in the practice of the subject matter as disclosed.

Nucleic acid and protein sequences for a number of Sapovirus isolates are also known. Representative Sapovirus sequences are presented in SEQ ID NOS:1, 7, 14, and 20. Additional representative sequences, including sequences of ORF1 and ORF2, and their encoded polypeptides from Sapovirus isolates are listed in the National Center for Biotechnology Information (NCBI) database. See, for example, GenBank entries: Sapovirus Mc10, GenBank Accession No. NC.010624; Sapporo virus, GenBank Accession No. U65427; Sapovirus Mc10, GenBank Accession No. AY237420; Sapovirus SaKaeo-15/Thailand, GenBank Accession No. AY646855; Sapporo virus, GenBank Accession No. NC.006269; Sapovirus C12, GenBank Accession No. NC 006554; Sapovirus C12, GenBank Accession No. AY603425; Sapovirus Hu/Dresden/pJG-Sap01/DE, GenBank Accession No. AY694184; Human calicivirus SLV/cruise ship/2000/USA, GenBank Accession No. AY289804; Human calicivirus SLV/Arg39, GenBank Accession No. AY289803; Porcine enteric calicivirus strain LL14, GenBank Accession No. AY425671; Porcine enteric calicivirus, GenBank Accession No. NC 000940; Human calicivirus strain Mc37, GenBank Accession No. AY237415; Mink enteric calicivirus strain Canada 151A, GenBank Accession No. AY144337; Human calicivirus SLV/Hou7-1181, GenBank Accession No. AF435814; Human calicivirus SLV/Mex14917/2000, GenBank Accession No. AF435813; Human calicivirus SLV/Mex340/1990, GenBank Accession No. AF435812; Porcine enteric calicivirus, GenBank Accession No. AF182760; Sapporo virus-London/29845, GenBank Accession No. U95645; Sapporo virus-Manchester, GenBank Accession No. X86560; Sapporo virus-Houston/86, GenBank Accession No. U95643; Sapporo virus-Houston/90, GenBank Accession No. U95644; and Human calicivirus strain HuCV/Potsdam/2000/DEU, GenBank Accession No. AF294739; all of which sequences (as entered by the date of filing of this application) are herein incorporated by reference.

As used herein, the terms "capsid protein" or "capsid polypeptide" or "VP1" in reference to a Sapovirus refer to a polypeptide comprising a sequence homologous or identical to the capsid polypeptide of a Sapovirus, and include sequences displaying at least about 80-99.9% sequence identity thereto, including any percent identity within these ranges, such as 81, 82, 83, 84, 85, 86, 87, 88, 89, 90, 91, 92, 93, 94, 95, 96, 97, 98, 99, 100% sequence identity thereto. The capsid polypeptide may be encoded by either ORF1 or ORF2 in different strains of Sapovirus. In some strains, the Sapovirus has two open reading frames: the capsid protein is encoded by ORF1 as part of a polyprotein and a minor structural protein (VP10) is encoded by ORF2. In other strains, the Sapovirus has three open reading frames: a stop codon precedes the coding region for the capsid protein, which is encoded by ORF2, and a minor structural protein (VP10) is encoded by ORF3.

As used herein, the terms "minor structural protein" or "minor structural polypeptide" or "VP10" in reference to a Sapovirus refer to a polypeptide comprising a sequence homologous or identical to the polypeptide encoded by the open reading frame following the coding region for the capsid protein in the Sapovirus genome (either ORF2 or ORF3 depending on the strain), and include sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99.9% sequence identity thereto.

As used herein, the term "Sapovirus polyprotein" refers to a polyprotein comprising a sequence homologous or identical to the ORF1-encoded polyprotein of a Sapovirus, and includes sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 99.9% sequence identity thereto.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but may be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term "antigen" denotes both subunit antigens (i.e., antigens which are separate and discrete from a whole organism with which the antigen is associated in nature), as well as, killed, attenuated or inactivated bacteria, viruses, fungi, parasites or other microbes. Antibodies such as anti-idiotype antibodies, or fragments thereof, and synthetic peptide mimotopes, which may mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

The term "antibody" encompasses polyclonal and monoclonal antibody preparations, as well as preparations including hybrid antibodies, altered antibodies, chimeric antibodies and, humanized antibodies, as well as: hybrid (chimeric) antibody molecules and any functional fragments obtained from such molecules, wherein such fragments retain specific-binding properties of the parent antibody molecule.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components. In particular, Sapovirus may be obtained from biological samples such as vomit or diarrhea from individuals infected with the viruses.

By "subject" is meant any member of the subphylum chordata, including, without limitation, humans and other primates, including non-human primates such as chimpanzees and other apes and monkey species; farm animals such as cattle, sheep, pigs, goats, deer and horses; domestic mammals such as dogs and cats; laboratory animals including rodents such as mice, rats and guinea pigs; birds, including domestic, wild and game birds such as chickens, turkeys and other gallinaceous birds, ducks, geese, wild and game animals, and the like. The term does not denote a particular age. Thus, both adult and newborn individuals are intended to be covered.

The terms "variant," "analog" and "mutein" refer to biologically active derivatives of the reference molecule that retain desired activity, such as antigenic activity in inducing an immune response against Sapovirus. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, and the like), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301). In embodiments, the analog or mutein has at least the same antigenic activity as the native molecule. Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic-aspartate and glutamate; (2) basic-lysine, arginine, histidine; (3) non-polar-alanine, valine, leucine, isoleucine, proline, phenylalanine, methionine, tryptophan; and (4) uncharged polar-glycine, asparagine, glutamine, cysteine, serine threonine, tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that may tolerate change by reference to Hopp/Woods and Kyte-Doolittle plots, well known in the art.

The term "multiple epitope fusion antigen" or "multiple epitope fusion protein" as used herein intends a polypeptide in which multiple Sapovirus antigens are part of a single, continuous chain of amino acids, which chain does not occur in nature. The Sapovirus antigens may be connected directly to each other by peptide bonds or may be separated by intervening amino acid sequences. The fusion antigens may contain ORF1-encoded, ORF2-encoded, and/or ORF3-encoded polypeptides or fragments thereof, including, for example, sequences of Sapovirus polypeptides, such as N-terminal protein, p11, p28, NTPase, p32, VPg, protease, polymerase, VP1, and VP10. The fusion antigens may also contain sequences exogenous to the Sapovirus. Moreover, the sequences present may be from multiple genotypes and/or isolates of Sapovirus.

By "therapeutically effective amount" in the context of the immunogenic compositions is meant an amount of an immunogen (e.g., immunogenic polypeptide, fusion protein, polyprotein, or nucleic acid encoding an antigen) which will induce an immunological response, either for antibody production or for treatment or prevention of Sapovirus infection. Such a response will generally result in the development in the subject of an antibody-mediated and/or a secretory or cellular immune response to the composition. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or γ, δ-T cell populations.

For purposes of the present disclosure, an "effective amount" of an adjuvant will be that amount which enhances an immunological response to a co-administered antigen or nucleic acid encoding an antigen.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

Before describing the present disclosure in detail, it is to be understood that the practice of the present disclosure will employ, unless otherwise indicated, conventional methods of virology, microbiology, molecular biology, recombinant DNA techniques and immunology all of which are within the ordinary skill of the art. Such techniques are explained fully in the literature. Although a number of methods and materials similar or equivalent to those described herein may be used in the practice of the present invention as claimed, the materials and methods are described herein.

The present disclosure includes compositions and methods for immunizing a subject against Sapovirus infection. The instant disclosure provides immunogenic compositions comprising nucleic acids encoding capsid proteins and/or other immunogenic polypeptides from one or more strains of Sapovirus, compositions comprising immunogenic polypeptides derived from one or more strains of Sapovirus. Immunogenic polypeptides to be used in the practice of the instant subject matter may include Sapovirus-derived polypeptides, including ORF1-encoded polypeptides, ORF2-encoded polypeptides, ORF3-encoded polypeptides, multiple epitope fusion antigens, and/or ORF1-encoded polyproteins. In addition, immunogenic compositions may comprise one or more adjuvants or nucleic acids encoding adjuvants, wherein immunogenic polypeptides are mixed or co-expressed with adjuvants. Immunogenic compositions may also comprise additional antigens other than Sapovirus antigens, such as antigens that may be used in immunization against pathogens that cause diarrheal diseases.

In order to further an understanding of the subject matter as disclosed, a more detailed discussion is provided below regarding the production of nucleic acids and polypeptides for use in immunogenic compositions and methods of using such compositions in the treatment or prevention of Sapovirus infection.

Structural Polypeptides, Nonstructural Polypeptides, and Polyproteins

The immunogenic compositions described herein may comprise one or more polypeptides derived from one or more genotypes and/or isolates of Sapovirus. Polypeptides that may be used in the practice of the subject matter as disclosed herein include structural proteins, nonstructural proteins, and polyproteins. Such polypeptides may be full-length proteins or variants or immunogenic fragments thereof capable of eliciting an immune response to a Sapovirus.

Cleavage of the Sapovirus strain Mc10 polyprotein, for example (GenBank Accession No. AY237420), by a 3C-like protease produces at least ten distinct products, p11, p28, p35 (NTPase), p32, p14 (VPg), p70 (Pro-Pol), p60 (VP1). Initial proteolytic processing produces p66 (p28-p35), p46 (p32-p14), and p120 (p32-p14-p70) fragments. The polyprotein comprises the polypeptides in the order of $NH_2$—p11-p28-NTPase-p32-VPg-p70(Pro-Pol)-VP1-COOH. The p70 (Pro-Pol) region of the polyprotein resides at residues 1056-1720, and the VP1 region of the polyprotein resides at residues 1721-2278 (numbered relative to GenBank Accession No. AY237420).

Nucleic acid and amino acid sequences of a number of Sapovirus strains and isolates, including nucleic acid and amino acid sequences of VP1 and VP10 structural proteins and the various regions of Sapovirus polyproteins, including p11, p28, NTPase, p32, VPg, p70(Pro-Pol), VP1 genes and polypeptides have also been determined.

The polypeptides in immunogenic compositions may be encoded by any region of a Sapovirus genome. Multiple polypeptides may be included in immunogenic compositions. Such compositions may comprise polypeptides from the same Sapovirus isolate or from different strains and isolates, including isolates having any of the various Sapovirus genotypes, to provide increased protection against a broad range of Sapovirus genotypes. Multiple viral strains of Sapovirus are known, and multiple polypeptides comprising epitopes derived from any of these strains may be used in immunogenic compositions.

The antigens used in the immunogenic compositions of the present disclosure may be present in the composition as individual separate polypeptides. Generally, the recombinant proteins of the present disclosure are expressed as a GST-fusion protein and/or a His-tagged fusion protein.

Multiepitope Fusion Proteins

The immunogenic compositions described herein may also comprise multiple epitope fusion proteins. See, e.g., International Publication No. WO 97/44469, U.S. Pat. Nos. 6,632,601, 6,630,298, 6,514,731, and 6,797,809; herein incorporated by reference in their entireties. Such fusion proteins include multiple epitopes derived from two or more viral polypeptides of one or more genotypes and/or isolates of Sapovirus. Multiple epitope fusion proteins offer two principal advantages: first, a polypeptide that may be unstable or poorly expressed on its own may be assisted by adding a suitable hybrid partner that overcomes the problem; second, commercial manufacture is simplified as only one expression and purification need be employed in order to produce two polypeptides which are both antigenically useful.

Multiepitope fusion proteins may contain one or more of the various domains of Sapovirus polyproteins, full-length polyproteins, VP1 (also referred to herein as a capsid protein) and/or VP10 (also referred to herein as a Sapovirus minor structural protein); or fragments thereof, derived from one or more Sapovirus isolates. The polypeptides in fusion proteins may be derived from the same Sapovirus isolate or from different strains and isolates, including isolates having any of the various Sapovirus genotypes, to provide increased protection against a broad range of Sapovirus genotypes. Multiple viral strains of Sapovirus are known, and epitopes derived from any of these strains may be used in a fusion protein.

It is well known that any given species of organism varies from one individual organism to another and further that a given organism such as a virus may have a number of different strains. For example, as explained above, Sapovirus includes at least five genogroups (G1-GV). Each strain includes a number of antigenic determinants that are in homologous regions present in all strains of Sapoviruses but are slightly different from one viral strain to another. Thus, a multiple epitope fusion antigen may include multiple polypeptides from different viral strains of Sapovirus, each comprising a particular homologous region but each having a different form of an antigenic determinant. In general, antigenic determinants may have a high degree of homology in terms of amino acid sequence, which degree of homology is generally 30% or more, 40% or more, when aligned. A fusion protein may also comprise multiple copies of an epitope, wherein one or more polypeptides of the fusion protein comprise sequences comprising exact copies of the same epitope. Additionally, polypeptides may be selected based on the particular viral clades endemic in specific geographic regions where vaccine compositions containing the fusions will be used. It is readily apparent that the subject fusions provide an effective means of treating Sapovirus infection in a wide variety of contexts.

Multiple epitope fusion antigens may be represented by the formula $NH_2$-A-$\{$-X-L-$\}_n$-B—COOH, wherein: X is an amino acid sequence of a Sapovirus antigen or a fragment thereof; L is an optional linker amino acid sequence; A is an optional N-terminal amino acid sequence; B is an optional C-terminal amino acid sequence; and n is 2, 3, 4, 5, 6, 7, 8, 9, 10, 11, 12, 13, 14 or 15.

If an -X- moiety has a leader peptide sequence in its wild-type form, this may be included or omitted in the multiple epitope fusion antigen. In some embodiments, the leader peptides will be deleted except for that of the -X- moiety located at the N-terminus of the hybrid protein i.e., the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of (-X-L-), linker amino acid sequence -L- may be present or absent. For instance, when n=2 the hybrid may be $NH_2$-$X_1$-$L_1$-$X_2$-$L_2$-COOH, $NH_2$-$X_1$-$X_2$-COOH, $NH_2$-$X_1$-$L_1$-$X_2$-COOH, $NH_2$-$X_1$-$X_2$-$L_2$-COOH, and the like. Linker amino acid sequence(s)-L- will typically be short, e.g., 20 or fewer amino acids (i.e., 20, 19, 18, 17, 16, 15, 14, 13, 12, 11, 10, 9, 8, 7, 6, 5, 4, 3, 2, 1). Examples include short peptide sequences which facilitate cloning, poly-glycine linkers (Gly, where n=2, 3, 4, 5, 6, 7, 8, 9, 10 or more), and histidine tags ($His_n$ where n=3, 4, 5, 6, 7, 8, 9, 10 or more). Other suitable linker amino acid sequences will be apparent to those skilled in the art. A useful linker is GSGGGG, with the Gly-Ser dipeptide being formed from a BamHI restriction site, which aids cloning and manipulation, and the $(Gly)_4$ tetrapeptide being a typical poly-glycine linker. In addition, protease substrate sequences may also be added (e.g., TEV protease: ENLYFQG).

-A- is an optional N-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking or short peptide sequences which facilitate cloning or purification (e.g., a histidine tag $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is an oligopeptide (e.g., with 1, 2, 3, 4, 5, 6, 7 or 8 amino acids) which provides a N-terminus methionine.

-B- is an optional C-terminal amino acid sequence. This will typically be short, e.g., 40 or fewer amino acids (i.e., 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g., $His_n$ where n=3, 4, 5, 6, 7, 8, 9, 10 or more), or sequences which enhance protein stability. Other suitable C-terminal amino acid sequences will be apparent to those skilled in the art, including that such $His_n$ sequences may be removed when a TEV protease substrate sequence precedes it (e.g., $ENLYFQGHis_n$).

The individual antigens of the immunogenic composition within the multiple epitope fusion antigen (individual -X- moieties) may be from one or more strains or from one or more M types. Where n=2, for instance, $X_2$ may be from the same strain or type as $X_1$ or from a different strain or type. Where n=3, the strains might be (i) $X_1$=$X_2$=$X_3$, (ii) $X_1$=$X_2$ not equal to $X_3$, (iii) $X_1$ not equal to $X_2$=$X_3$, (iv) $X_1$ not equal to $X_2$ not equal to $X_3$, or (v) $X_1$=$X_3$ not equal to $X_2$, and the like.

Where multiple epitope fusion antigens are used, the individual antigens within the fusion protein (i.e., individual -X- moieties) may be from one or more strains. Where n=2, for instance, $X_2$ may be from the same strain as $X_1$ or from a different strain. Where n=3, the strains might be (i) $X_1$=$X_2$=$X_3$ (ii) X1=$X_2$ not equal to $X_3$ (iii) $X_1$ not equal to $X_2$=$X_3$ (iv) $X_1$ not equal to $X_2$ not equal to $X_3$ or (v) X1=$X_3$ not equal to $X_2$, and the like.

Accordingly, in embodiments, antigenic determinants from different Sapovirus strains may be present. Representative multiepitope fusion proteins for use in the present disclosure, comprising polypeptides derived from Sapovirus isolates, are discussed below. However, it is to be understood that multiepitope fusion proteins comprising other epitopes derived from Sapovirus genomes or multiepitope fusion proteins comprising different arrangements of epitopes will also find use in immunogenic compositions as disclosed.

In certain embodiments, the fusion protein comprises one or more capsid and/or minor structural polypeptides from one or more isolates of Sapovirus.

In another embodiment, the fusion protein comprises VP1 polypeptides from more than one Sapovirus strain (e.g., $VP1_{Sapporo}$-$VP1_{London}$/29845, $VP1_{London}$/29845-$VP1_{Manchester}$-$VP1_{Sapporo}$, $VP1_{Manchester}$-$VP1_{Parkville}$-$VP1_{Sapporo}$-$VP1_{London}$/29845, $VP1_{Parkville}$-$VP1_{Houston}$/90-$VP1_{Houston}$/86-VP $1_{Manchester}$-VP $1_{Sapporo}$).

In all fusions described herein, the viral regions need not be in the order in which they occur naturally. Moreover, each of the regions may be derived from the same or different Sapovirus isolates. The various Sapovirus polypeptides present in the various fusions described above may either be full-length polypeptides or portions thereof.

If desired, the fusion proteins, or the individual components of these proteins, also may contain other amino acid sequences, such as amino acid linkers or signal sequences, as well as ligands useful in protein purification, such as glutathione-S-transferase and staphylococcal protein A.

Nucleic Acids

Nucleic acids for use as disclosed herein, for example, in polypeptide production, may be derived from any of the various regions of a Sapovirus genome, including from any of the ORF1, ORF2, or ORF3 regions. Representative sequences from Sapovirus isolates are listed herein. Thus, nucleic acids for use as disclosed herein include those derived from one or more sequences from any pathogenic Sapovirus genotype or isolate.

Representative sequences from Sapovirus are known, including SEQ ID NOs:1, 7, 14, and 20. Representative Sapovirus sequences are Sapporo virus-London/29845, GenBank Accession No. U95645, Parkville virus, GenBank Accession No. AF294739; and Sapporo virus-Houston/86, GenBank Accession No. U95643.

Any of these sequences, as well as fragments and variants thereof that may be used in nucleic acid immunization to elicit an immune response to a Sapovirus will find use in the present methods. Thus, the present disclosure provides variants of the above sequences displaying at least about 80-100% sequence identity thereto, including any percent identity within these ranges, such as 81, 82, 83, 84, 85, 86, 87, 88, 89, 90, 91, 92, 93, 94, 95, 96, 97, 98, 99, 99.9% sequence identity thereto. The present disclosure also provides polynucleotides encoding immunogenic fragments of a Sapovirus polypeptide derived from any of the above sequences or a variant thereof. Polynucleotides may also comprise coding sequences for polypeptides which occur naturally or may be artificial sequences which do not occur in nature.

Polynucleotides may contain less than an entire Sapovirus genome, or alternatively may include the sequence of an entire viral genomic RNA. For example, polynucleotides may comprise one or more sequences from the ORF1, ORF2, and ORF3 regions of a Sapovirus genome. Polynucleotides may also comprise the entire viral genomic RNA or less than the entire viral genomic RNA from multiple genotypes and/or isolates of Sapovirus.

In embodiments, polynucleotides comprise an ORF1 sequence coding for the full-length polyprotein of a Sapovirus. In other embodiments, polynucleotides comprise one or more portions of the ORF1 sequence of a Sapovirus.

In another example, a polynucleotide may comprise a nucleotide sequence encoding a portion of a Sapovirus polyprotein.

In embodiments, the polynucleotides comprise sequences encoding one or more capsid proteins of a Sapovirus. For example, polynucleotides may comprise one or more sequences coding for structural proteins (e.g., VP1, VP2, VP10) of a Sapovirus. In certain embodiments, polynucleotides comprise sequences coding for at least two capsid proteins from multiple genotypes and/or isolates of Sapovirus.

In embodiments, polynucleotides comprise one or more Sapovirus sequences coding for the capsid proteins of one or more isolates of Sapovirus. In certain embodiments, polynucleotides comprise one or more sequences coding for the capsid proteins of one or more isolates of Sapovirus.

In embodiments, the present disclosure provides polynucleotides encoding a multiepitope fusion protein as described herein. Multiepitope fusion proteins may comprise sequences from one or more genotypes and/or isolates of Sapovirus.

Nucleic acids according to the instant disclosure may be prepared in many ways (e.g., by chemical synthesis, from genomic or cDNA libraries, from the organism itself, etc.) and may take various forms (e.g., single stranded, double stranded, vectors, probes, and the like). In embodiments, nucleic acids are prepared in substantially pure form (i.e., substantially free from other host cell or non-host cell nucleic acids).

For example, nucleic acids may be obtained by screening cDNA and/or genomic libraries from cells infected with virus, or by deriving the gene from a vector known to include the same. For example, polynucleotides of interest may be isolated from a genomic library derived from viral RNA, present in, for example, stool or vomit samples from an infected individual. Alternatively, Sapovirus nucleic acids may be isolated from infected humans or other mammals or from stool or vomit samples collected from infected individuals. Viruses may be grown in LLC-PK cells in the presence of intestinal fluid containing bile acids. An amplification method such as PCR may be used to amplify polynucleotides from either Sapovirus genomic RNA or cDNA encoding therefor. Alternatively, polynucleotides may be synthesized in the laboratory, for example, using an automatic synthesizer. The nucleotide sequence may be designed with the appropriate codons for the particular amino acid sequence desired. In general, one will select preferred codons for the intended host in which the sequence will be expressed. The complete sequence of the polynucleotide of interest may be assembled from overlapping oligonucleotides prepared by standard methods and assembled into a complete coding sequence. The polynucleotides may be RNA or single- or double-stranded DNA. In embodiments, the polynucleotides are isolated free of other components, such as proteins and lipids.

Thus, particular nucleotide sequences may be obtained from vectors harboring the desired sequences or synthesized completely or in part using various oligonucleotide synthesis techniques known in the art, such as site-directed mutagenesis and polymerase chain reaction (PCR) techniques where appropriate. In particular, one method of obtaining nucleotide sequences encoding the desired sequences is by annealing complementary sets of overlapping synthetic oligonucleotides produced in a conventional, automated polynucleotide synthesizer, followed by ligation with an appropriate DNA ligase and amplification of the ligated nucleotide sequence via PCR.

Production of Immunogenic Polypeptides

Polypeptides described herein may be prepared in any suitable manner (e.g., recombinant expression, purification from cell culture, chemical synthesis, and the like) and in various forms (e.g., native, fusions, non-glycosylated, lipidated, and the like). Such polypeptides include naturally-occurring polypeptides, recombinantly produced polypeptides, synthetically produced polypeptides, or polypeptides produced by a combination of these methods. Means for preparing such polypeptides are well understood in the art. Polypeptides are prepared in substantially pure form (i.e., substantially free from other host cell or non-host cell proteins).

Polypeptides may be conveniently synthesized chemically, by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid may then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like. Typical solid supports are cross-linked polymeric supports. These may include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptides of the present disclosure may also be chemically prepared by other methods such as by the method of simultaneous multiple peptide synthesis.

Alternatively, the above-described immunogenic polypeptides, polyproteins, and multiepitope fusion proteins may be produced recombinantly. Once coding sequences for the desired proteins have been isolated or synthesized, they may be cloned into any suitable vector or replicon for expression. Numerous cloning vectors are known to those of skill in the art, and the selection of an appropriate cloning vector is a matter of choice. A variety of bacterial, yeast, plant, mammalian and insect expression systems are available in the art and any such expression system may be used. Optionally, a polynucleotide encoding these proteins may be translated in a cell-free translation system. Such methods are well known in the art.

Examples of recombinant DNA vectors for cloning and host cells which they may transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells).

Insect cell expression systems, such as baculovirus systems, may also be used and are known to those of skill in the art and described in, e.g., Summers and Smith, Texas Agricultural Experiment Station Bulletin No. 1555 (1987). Materials and methods for baculovirus/insect cell expression systems are commercially available in kit form from, inter alia, Invitrogen, San Diego, CA ("MaxBac" kit).

Plant expression systems may also be used to produce the immunogenic proteins. Generally, such systems use virus-based vectors to transfect plant cells with heterologous genes.

Viral systems, such as a vaccinia based infection/transfection system, will also find use with the subject matter as disclosed herein. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation product(s).

The gene may be placed under the control of a promoter, ribosome binding site (for bacterial expression) and, optionally, an operator (collectively referred to herein as "control" elements), so that the DNA sequence encoding the desired immunogenic polypeptide is transcribed into RNA in the host cell transformed by a vector containing this expression construction. The coding sequence may or may not contain a signal peptide or leader sequence. With the present subject matter as disclosed herein, both the naturally occurring signal peptides or heterologous sequences may be used. Leader sequences may be removed by the host in post-translational processing. See, e.g., U.S. Pat. Nos. 4,431,739; 4,425,437; 4,338,397, each herein incorporated by reference in their entireties. Such sequences include, but are not limited to, the tpa leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound.

Other types of regulatory elements may also be present in the vector, for example, enhancer sequences.

The control sequences and other regulatory sequences may be ligated to the coding sequence prior to insertion into a vector. Alternatively, the coding sequence may be cloned directly into an expression vector which already contains the control sequences and an appropriate restriction site.

In embodiments, it may be necessary to modify the coding sequence so that it may be attached to the control sequences with the appropriate orientation; i.e., to maintain the proper reading frame. It may also be desirable to produce mutants or analogs of the immunogenic polypeptides. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), as well as others. Similarly, bacterial hosts such as *E. coli, Bacillus subtilis*, and *Streptococcus* spp., will find use with the present expression constructs. Yeast hosts useful with the subject matter as disclosed include, inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni*.

Depending on the expression system and host selected, the proteins as disclosed herein are produced by growing host cells transformed by an expression vector described above under conditions whereby the protein of interest is expressed. The selection of the appropriate growth conditions is within the skill of the art. The cells are then disrupted, using chemical, physical or mechanical means, which lyse the cells yet keep the Sapovirus immunogenic polypeptides substantially intact. Intracellular proteins may also be obtained by removing components from the cell wall or membrane, e.g., by the use of detergents or organic solvents, such that leakage of the immunogenic polypeptides occurs.

For example, methods of disrupting cells for use with the subject matter as disclosed herein include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Sapovirus immunogenic polypeptides are further purified, using standard purification techniques such as but not limited to, column chromatography, ion-exchange chromatography, size-exclusion chromatography, electrophoresis, HPLC, immunoabsorbent techniques, affinity chromatography, immunoprecipitation, and the like.

For example, one method for obtaining the intracellular Sapovirus immunogenic polypeptides as disclosed herein involves affinity purification, such as by immunoaffinity chromatography using specific antibodies. The choice of a suitable affinity resin is within the skill in the art. After affinity purification, immunogenic polypeptides may be further purified using conventional techniques well known in the art, such as by any of the techniques described above.

It may be desirable to produce multiple polypeptides simultaneously (e.g., structural and/or nonstructural proteins from one or more viral strains or viral polypeptides in combination with polypeptide adjuvants). Production of two or more different polypeptides may readily be accomplished by e.g., co-transfecting host cells with constructs encoding the different polypeptides. Co-transfection may be accomplished either in trans or cis, i.e., by using separate vectors or by using a single vector encoding the polypeptides. If a single vector is used, expression of the polypeptides may be driven by a single set of control elements or, alternatively, the sequences coding for the polypeptides may be present on the vector in individual expression cassettes, regulated by individual control elements.

The polypeptides described herein may be attached to a solid support. The solid supports which may be used in the practice with the subject matter as disclosed herein include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more Sapovirus antigens) under suitable binding conditions such that the component is sufficiently immobilized to the support. Sometimes, immobilization of the antigen to the support may be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that may be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art.

If desired, polypeptides may be labeled using conventional techniques. Suitable labels include fluorophores, chromophores, radioactive atoms (particularly $^{32}P$ and $^{125}I$, electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. A single label or a combination of labels may be used in the as disclosed herein.

Once formulated, the compositions as disclosed herein may be administered directly to the subject (e.g., as described above) or, alternatively, delivered ex vivo, to cells derived from the subject, using methods such as those described above.

Immunogenic Compositions

The present disclosure also provides compositions comprising one or more of the immunogenic polypeptides and/or polyproteins multiepitope fusion proteins described herein. Different polypeptides, polyproteins, and multiple epitope fusion proteins may be mixed together in a single formulation. Within such combinations, an antigen of the immunogenic composition may be present in more than one polypeptide, or multiple epitope polypeptide, or polyprotein. In one aspect, Sapovirus VP1 comprising immunogenic compositions include lysates from baculovirus expressed insect host cells. In a related aspect, said lysates undergo various levels of fractionation or are unfractionated, where the expressed protein is modified or unmodified from its expressed state (e.g., $His_n$ tag intact).

The immunogenic compositions may comprise a mixture of polypeptides, which in turn may be delivered using the same or different vehicles. Antigens may be administered individually or in combination, in e.g., prophylactic (i.e., to prevent infection) or therapeutic (to treat infection) immunogenic compositions. The immunogenic composition may be given more than once (e.g., a "prime" administration followed by one or more "boosts") to achieve the desired effects. The same composition may be administered in one or more priming and one or more boosting steps. Alternatively, different compositions may be used for priming and boosting.

The immunogenic compositions will generally include one or more "pharmaceutically acceptable excipients or vehicles" such as water, saline, glycerol, ethanol, and the like. Additionally, auxiliary substances, such as wetting or emulsifying agents, pH buffering substances, and the like, may be present in such vehicles.

Immunogenic compositions will typically, in addition to the components mentioned above, comprise one or more "pharmaceutically acceptable carriers." These include any carrier which does not itself induce the production of antibodies harmful to the individual receiving the composition. Suitable carriers typically are large, slowly metabolized macromolecules such as proteins, polysaccharides, polylactic acids, polyglycolic acids, polymeric amino acids, amino acid copolymers, and lipid aggregates (such as oil droplets or liposomes). Such carriers are well known to those of ordinary skill in the art. A composition may also contain a diluent, such as water, saline, glycerol, and the like. Additionally, an auxiliary substance, such as a wetting or emulsifying agent, pH buffering substance, and the like, may be present. A thorough discussion of pharmaceutically acceptable components is available in Gennaro (2000) Remington: The Science and Practice of Pharmacy. 20th ed., ISBN: 0683306472.

Pharmaceutically acceptable salts may also be used in compositions as disclosed herein, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions as disclosed may also contain liquids or excipients, such as water, saline, glycerol, dextrose, ethanol, or the like, singly or in combination, as well as substances such as wetting agents, emulsifying agents, or pH buffering agents. Antigens may also be adsorbed to, entrapped within or otherwise associated with liposomes and particulate carriers such as PLG.

Antigens may be conjugated to a carrier protein in order to enhance immunogenicity. This is particularly useful in compositions in which a saccharide or carbohydrate antigen is used.

Carrier proteins may include, but are not limited to, bacterial toxins or toxoids, such as diphtheria or tetanus toxoids. The $CRM_{197}$ diphtheria toxoid may be used. Other carrier polypeptides include the *N. meningitidis* outer membrane protein (EP-A-0372501), synthetic peptides (EP-A-0378881 and EP-A-0427347), heat shock proteins (WO 93/17712 and WO 94/03208), pertussis proteins (WO 98/58668 and EP-A-0471177), protein D from *H. influenzae* (WO 00/56360), cytokines (WO 91/01146), lymphokines, hormones, growth factors, toxin A or B from *C. difficile* (WO 00/61761), iron-uptake proteins, such as transferring (WO 01/72337), etc. Where a mixture comprises capsular saccharide from both serigraphs A and C, it may be that the ratio (w/w) of MenA saccharide:MenC saccharide is greater than 1 (e.g., 2:1, 3:1, 4:1, 5:1, 10:1 or higher). Different saccharides may be conjugated to the same or different type of carrier protein. Any suitable conjugation reaction may be used, with any suitable linker where necessary.

Immunogenic compositions, including vaccines as disclosed may be administered in conjunction with other immunoregulatory agents. For example, a vaccine as disclosed herein may include an adjuvant. Adjuvants include, but are not limited to, one or more of the following types of adjuvants described below.

Mineral Containing Compositions

Mineral containing compositions suitable for use as adjuvants disclosed herein include mineral salts, such as aluminum salts and calcium salts. Salts as disclosed herein includes mineral salts such as hydroxides (e.g., oxyhydroxides), phosphates (e.g., hydroxyphosphates, orthophosphates), sulfates, and the like, or mixtures of different mineral compounds (e.g., a mixture of a phosphate and a hydroxide adjuvant, optionally with an excess of the phosphate), with the compounds taking any suitable form (e.g., gel, crystalline, amorphous, and the like). The mineral containing compositions may also be formulated as a particle of metal salt (WO00/23105).

Aluminum salts may be included in vaccines such that the dose of $Al^{3+}$ is between 0.2 and 1.0 mg per dose.

In embodiments, the aluminum based adjuvant for use as disclosed is alum (aluminum potassium sulfate $(AlK(SO_4)_2)$), or an alum derivative, such as that formed in-situ by mixing an antigen in phosphate buffer with alum, followed by titration and precipitation with a base such as ammonium hydroxide or sodium hydroxide.

Another aluminum-based adjuvant for use in vaccine formulations of the present invention is aluminum hydroxide adjuvant $(Al(OH)_3)$ or crystalline aluminum oxyhydroxide (AlOOH), which is an excellent adsorbant, having a surface area of approximately 500 $m^2/g$. Alternatively, aluminum phosphate adjuvant $(AlPO_4)$ or aluminum hydroxyphosphate, which contains phosphate groups in place of some or all of the hydroxyl groups of aluminum hydroxide adjuvant is provided. In embodiments, aluminum phosphate adjuvants provided herein are amorphous and soluble in acidic, basic and neutral media.

In embodiments, the adjuvant as disclosed herein comprises both aluminum phosphate and aluminum hydroxide. In one aspect, the adjuvant has a greater amount of aluminum phosphate than aluminum hydroxide, such as a ratio of 2:1, 3:1, 4:1, 5:1, 6:1, 7:1, 8:1, 9:1 or greater than 9:1, by weight aluminum phosphate to aluminum hydroxide. More particular still, aluminum salts in the vaccine are present at 0.4 to 1.0 mg per vaccine dose, or 0.4 to 0.8 mg per vaccine dose, or 0.5 to 0.7 mg per vaccine dose, or about 0.6 mg per vaccine dose.

Generally, the aluminum-based adjuvant(s), or ratio of multiple aluminum-based adjuvants, such as aluminum phosphate to aluminum hydroxide is selected by optimization of electrostatic attraction between molecules such that the antigen carries an opposite charge as the adjuvant at the desired pH. For example, aluminum phosphate adjuvant (iep=4) adsorbs lysozyme, but not albumin at pH 7.4. Should albumin be the target, aluminum hydroxide adjuvant would be selected (i.e., 11.4). Alternatively, pretreatment of aluminum hydroxide with phosphate lowers its isoelectric point, making it a preferred adjuvant for more basic antigens.

Oil-Emulsions

Oil-emulsion compositions suitable for use as adjuvants may include squalene-water emulsions, such as MF59 (5% Squalene, 0.5% TWEEN 80™, and 0.5% SPAN 85™, formulated into submicron particles using a microfluidizer). See WO90/14837. MF59 is used as the adjuvant in the FLUAD™ influenza virus trivalent subunit vaccine.

Particularly adjuvants for use in the compositions are submicron oil-in-water emulsions. Submicron oil-in-water emulsions for use herein may be squalene/water emulsions optionally containing varying amounts of MTP-PE, such as a submicron oil-in-water emulsion containing 4-5% w/v squalene, 0.25-1.0% w/v TWEEN 80™ (polyoxyelthylene-sorbitan monooleate), and/or 0.25-1.0% SPAN85™ (sorbitan trioleate), and, optionally, N-acetylmuramyl-L-alanyl-D-isogluatminyl-L-alanine-2-(.beta.-2'-dipalmito-yl-sn-glycero-3-huydroxyphosphphoryloxy)-ethylamine (MTP-PE), for example, the submicron oil-in-water emulsion known as "MF59" (International Publication No. WO90/14837; U.S. Pat. Nos. 6,299,884 and 6,451,325.) MF59 contains 4-5% w/v Squalene (e.g., 4.3%), 0.25-0.5% w/v TWEEN 80™, and 0.5% w/v SPAN 85™ and optionally contains various amounts of MTP-PE, formulated into submicron particles using a microfluidizer such as Model 110Y microfluidizer (Microfluidics, Newton, Mass.). For example, MTP-PE may be present in an amount of about 0-500 μg/dose, 0-250 μg/dose and 0-100 μg/dose. As used herein, the term "MF59-0" refers to the above submicron oil-in-water emulsion lacking MTP-PE, while the term MF59-MTP denotes a formulation that contains MTP-PE. For instance, "MF59-100" contains 100.mu.g MTP-PE per dose, and so on. MF69, another submicron oil-in-water emulsion for use herein, contains 4.3% w/v squalene, 0.25% w/v TWEEN 80™, and 0.75% w/v SPAN85™ and optionally MTP-PE. Yet another submicron oil-in-water emulsion is MF75, also known as SAF, containing 10% squalene, 0.4% TWEEN 80™, 5% pluronic-blocked polymer L121, and thr-MDP, also microfluidized into a submicron emulsion. MF75-MTP denotes an MF75 formulation that includes MTP, such as from 100-400 μg MTP-PE per dose.

Submicron oil-in-water emulsions, methods of making the same and immunostimulating agents, such as muramyl peptides, for use in the compositions, are described in detail in International Publication No. WO90/14837 and U.S. Pat. Nos. 6,299,884 and 6,451,325.

Complete Freund's adjuvant (CFA) and incomplete Freund's adjuvant (IFA) may also be used as adjuvants.

Saponin Formulations

Saponin formulations, may also be used as adjuvants. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponins may also be commercially obtained from *Smilax ornata* (sarsaprilla), Gypsophilla *paniculata* (brides veil), and *Saponaria officianalis* (soap root). Saponin adjuvant formulations include purified formulations, such as QS21, as well as lipid formulations, such as ISCOMs.

Saponin compositions have been purified using High Performance Thin Layer Chromatography (HP-TLC) and Reversed Phase High Performance Liquid Chromatography (RP-HPLC). Specific purified fractions using these techniques have been identified, including QS7, QS17, QS18, QS21, QH-A, QH-B and QH-C. In embodiments, the saponin is QS21. A method of production of QS21 is disclosed in U.S. Pat. No. 5,057,540. Saponin formulations may also comprise a sterol, such as cholesterol (see WO96/33739).

Combinations of saponins and cholesterols may be used to form unique particles called Immunostimulating Complexes (ISCOMs). ISCOMs typically also include a phospholipid such as phosphatidylethanolamine or phosphatidylcholine. Any known saponin may be used in ISCOMs. In embodiments, the ISCOM includes one or more of Quil A, QHA and QHC. ISCOMs are further described in EP0109942, WO96/11711 and WO96/33739. Optionally, the ISCOMS may be devoid of (an) additional detergent(s). See WO00/07621.

Bacterial or Microbial Derivatives

Adjuvants suitable for use as disclosed herein include bacterial or microbial derivatives such as:

(1) Non-Toxic Derivatives of Enterobacterial Lipopolysaccharide (LPs)

Such derivatives include Monophosphoryl lipid A (MPL) and 3-O-deacylated MPL (3dMPL). 3dMPL is a mixture of 3 De-O-acylated monophosphoryl lipid A with 4, 5 or 6 acylated chains. One "small particle" form of 3 De-O-acylated monophosphoryl lipid A is disclosed in EP 0 689 454. Such "small particles" of 3dMPL are small enough to be sterile filtered through a 0.22 micron membrane (see EP 0 689 454). Other non-toxic LPS derivatives include monophosphoryl lipid A mimics, such as aminoalkyl glucosaminide phosphate derivatives e.g., RC-529.

(2) Lipid A Derivatives

Lipid A derivatives include derivatives of lipid A from *Escherichia coli* such as OM-174.

(3) Immunostimulatory Oligonucleotides

Immunostimulatory oligonucleotides suitable for use as adjuvants may include nucleotide sequences containing a CpG motif (a sequence containing an unmethylated cytosine followed by guanosine and linked by a phosphate bond). Bacterial double stranded RNA or oligonucleotides containing palindromic or poly(dG) sequences have also been shown to be immunostimulatory.

The CpG's may include nucleotide modifications/analogs such as phosphorothioate modifications and may be double-stranded or single-stranded. Optionally, the guanosine may be replaced with an analog such as 2'-deoxy-7-deazaguanosine.

The CpG sequence may be directed to TLR9, such as the motif GTCGTT or TTCGTT.

The CpG sequence may be specific for inducing a Th1 immune response, such as a CpG-A ODN, or it may be more specific for inducing a B cell response, such a CpG-B ODN. In embodiments, the CpG is a CpG-A ODN.

In embodiments, the CpG oligonucleotide may be constructed so that the 5' end is accessible for receptor recognition. Optionally, two CpG oligonucleotide sequences may be attached at their 3' ends to form "immunomers."

(4) ADP-Ribosylating Toxins and Detoxified Derivatives Thereof.

Bacterial ADP-ribosylating toxins and detoxified derivatives thereof may be used as adjuvants. In embodiments, the protein may be derived from *E. coli* (i.e., *E. coli* heat labile enterotoxin "LT"), cholera ("CT"), or pertussis ("PT"). The use of detoxified ADP-ribosylating toxins as mucosal adjuvants is described in WO95/17211 and as parenteral adjuvants in WO98/42375. In embodiments, the adjuvant is a detoxified LT mutant such as LT-K63, LT-R72, and LTR192G.

Bioadhesives and Mucoadhesives

Bioadhesives and mucoadhesives may also be used as adjuvants. Suitable bioadhesives include esterified hyaluronic acid microspheres or mucoadhesives such as cross-linked derivatives of polyacrylic acid, polyvinyl alcohol, polyvinyl pyrollidone, polysaccharides and carboxymethylcellulose. Chitosan and derivatives thereof may also be used as adjuvants. E.g., WO99/27960.

Muramyl Peptides

Examples of muramyl peptides suitable for use as adjuvants include N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-s-n-glycero-3-hydroxyphosphoryloxy)-ethylamine MTP-PE).

Imidazoquinoline Compounds.

Examples of imidazoquinoline compounds suitable for use as adjuvants include Imiquimod and its analogues (see, e.g., U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612).

Thiosemicarbazone Compounds.

Examples of thiosemicarbazone compounds, as well as methods of formulating, manufacturing, and screening for compounds all suitable for use as adjuvants include those described in WO04/60308. The thiosemicarbazones are particularly effective in the stimulation of human peripheral blood mononuclear cells for the production of cytokines, such as TNF-α.

Tryptanthrin Compounds.

Examples of tryptanthrin compounds, as well as methods of formulating, manufacturing, and screening for compounds all suitable for use as adjuvants as disclosed herein include those described in WO04/64759. The tryptanthrin compounds are particularly effective in the stimulation of human peripheral blood mononuclear cells for the production of cytokines, such as TNF-α.

Combinations of aspects of one or more of the adjuvants identified above may be applied to the compositions as disclosed herein. For example, the following adjuvant compositions may be used:

(1) a saponin and an oil-in-water emulsion (WO99/11241); (2) a saponin (e.g., QS21)+a non-toxic LPS derivative (e.g., 3dMPL) (see WO94/00153); (3) a saponin (e.g., QS21)+a non-toxic LPS derivative (e.g., 3dMPL)+a cholesterol; (4) a saponin (e.g., QS21)+3dMPL+IL-12 (optionally+a sterol) (WO98/57659); (5) combinations of 3dMPL with, for example, QS21 and/or oil-in-water emulsions (See European patent applications 0835318, 0735898 and 0761231); (6) SAF, containing 10% Squalane, 0.4%

TWEEN80™, 5% pluronic-block polymer L121, and thr-MDP, either microfluidized into a submicron emulsion or vortexed to generate a larger particle size emulsion. (7) RIBI™ adjuvant system (RAS), (Ribi Immunochem) containing 2% Squalene, 0.2% TWEEN 80™, and one or more bacterial cell wall components from the group consisting of monophosphorylipid A (MPL), trehalose dimycolate (TDM), and cell wall skeleton (CWS), MPL+CWS (DE-TOX™); and (8) one or more mineral salts (such as an aluminum salt)+a non-toxic derivative of LPS (such as 3dPML). (9) one or more mineral salts (such as an aluminum salt) and one or more immunostimulatory oligonucleotides (such as a nucleotide sequence including a CpG motif) and one or more detoxified ADP-ribosylating toxins (such as LT-K63 and LT-R72).

Additional Antigens

Compositions of the as disclosed herein optionally may comprise one or more additional polypeptide antigens which are not derived from Sapovirus proteins. Such antigens include bacterial, viral, or parasitic antigens.

In some embodiments, a Sapovirus antigen is combined with one or more antigens including, but not limited to, antigens derived from a bacteria or virus, such as Orthomyxovirus (*influenza*), Pneumovirus (RSV), Paramyxovirus (PIV and Mumps), Morbillivirus (measles), Togavirus (Rubella), Enterovirus (polio), HBV, Coronavirus (SARS), and Varicella-zoster virus (VZV), Epstein Barr virus (EBV), *Streptococcus pneumoniae, Neisseria meningitides, Streptococcus pyogenes* (Group A *Streptococcus*), *Moraxella catarrhalis, Bordetella pertussis, Staphylococcus aureus, Clostridium tetani* (Tetanus), *Corynebacterium diphtheriae* (Diphtheria), *Haemophilus influenzae* B (Hib), *Pseudomonas aeruginosa, Streptococcus agalactiae* (Group B *Streptococcus*), and *E. coli.*

In other embodiments, a Sapovirus antigen is combined with one or more antigens including, but not limited to, *Neisseria meningitides, Streptococcus pneumoniae, Streptococcus pyogenes* (Group A *Streptococcus*), *Moraxella catarrhalis, Bordetella pertussis, Staphylococcus aureus, Staphylococcus epidermis, Clostridium tetani* (Tetanus), *Corynebacterium diphtheriae* (Diphtheria), *Haemophilus influenzae* B (Hib), *Pseudomonas aeruginosa, Legionella pneumophila, Streptococcus agalactiae* (Group B *Streptococcus*), *Enterococcus faecalis, Helicobacter pylori, Clamydia pneumoniae*, Orthomyxovirus (*influenza*), Pneumovirus (RSV), Paramyxovirus (PIV and Mumps), Morbillivirus (measles), Togavirus (Rubella), Enterovirus (polio), HBV, Coronavirus (SARS), Varicella-zoster virus (VZV), Epstein Barr virus (EBV), Cytomegalovirus (CMV).

In other embodiments, a Sapovirus antigen is combined with one or more antigens which are useful in a vaccine designed to protect individuals against pathogens that cause diarrheal diseases. Such antigens include, but are not limited to, rotavirus, *Shigella* spp., enterotoxigenic *Escherichia coli* (ETEC), *Vibrio cholerae*, and *Campylobacter jejuni* antigens. In embodiments, one or more Norovirus antigens may be derived from Norwalk virus, Snow Mountain virus, and/or Hawaii virus are combined with a rotavirus antigen in an immunogenic composition.

Antigens which may find use with the present compositions include, but are not limited to, one or more of the following antigens set forth below, or antigens derived from one or more of the pathogens set forth below:

Bacterial Antigens

Suitable Bacterial antigens as disclosed herein include proteins, polysaccharides, lipopolysaccharides, and outer membrane vesicles which may be isolated, purified or derived from a bacteria. In addition, bacterial antigens may include bacterial lysates and inactivated bacteria formulations. Bacteria antigens may be produced by recombinant expression. Bacterial antigens include epitopes which may be exposed on the surface of the bacteria during at least one stage of its life cycle. Bacterial antigens may be conserved across multiple serotypes. Bacterial antigens include antigens derived from one or more of the bacteria set forth below as well as the specific antigens examples identified below.

*Neisseria meningitides: Meningitides* antigens may include proteins (such as those identified in References 1-7), saccharides (including a polysaccharide, oligosaccharide or lipopolysaccharide), or outer-membrane vesicles purified or derived from *N. meningitides* serogroup such as A, C, W135, Y, and/or B. *Meningitides* protein antigens may be selected from adhesions, autotransporters, toxins, Fe acquisition proteins, and membrane associated proteins (e.g., integral outer membrane protein).

*Streptococcus pneumoniae: Streptococcus pneumoniae* antigens may include a saccharide (including a polysaccharide or an oligosaccharide) and/or protein from *Streptococcus pneumoniae*. Saccharide antigens may be selected from serotypes 1, 2, 3, 4, 5, 6B, 7F, 8, 9N, 9V, 10A, 11A, 12F, 14, 15B, 17F, 18C, 19A, 19F, 20, 22F, 23F, and 33F. Protein antigens may be selected from a protein identified in WO 98/18931, WO 98/18930, U.S. Pat. Nos. 6,699,703, 6,800,744, WO 97/43303, and WO 97/37026. *Streptococcus pneumoniae* proteins may be selected from the Poly Histidine Triad family (PhtX), the Choline Binding Protein family (CbpX), CbpX truncates, LytX family, LytX truncates, CbpX truncate-LytX truncate chimeric proteins, pneumolysin (Ply), PspA, PsaA, Sp128, Sp101, Sp130, Sp125 or Sp133.

*Streptococcus pyogenes* (Group A *Streptococcus*): Group A *Streptococcus* antigens may include a protein identified in WO 02/34771 or WO 2005/032582 (including GAS 40), fusions of fragments of GAS M proteins (including those described in WO 02/094851), fibronectin binding protein (Sfb1), Streptococcal heme-associated protein (Shp), and Streptolysin S (SagA).

*Moraxella catarrhalis: Moraxella* antigens include antigens identified in WO 02/18595 and WO 99/58562, outer membrane protein antigens (HMW-OMP), C-antigen, and/or LPS.

*Bordetella pertussis*: Pertussis antigens include pertussis holotoxin (PT) and filamentous haemagglutinin (FHA) from *B. pertussis*, optionally also combination with pertactin and/or agglutinogens 2 and 3 antigen.

*Staphylococcus aureus*: Staph *aureus* antigens include *S. aureus* type 5 and 8 capsular polysaccharides optionally conjugated to nontoxic recombinant *Pseudomonas aeruginosa* exotoxin A, such as STAPHVAX™, or antigens derived from surface proteins, invasins (leukocidin, kinases, hyaluronidase), surface factors that inhibit phagocytic engulfment (capsule, Protein A), carotenoids, catalase production, Protein A, coagulase, clotting factor, and/or membrane-damaging toxins (optionally detoxified) that lyse eukaryotic cell membranes (hemolysins, leukotoxin, leukocidin).

*Staphylococcus epidermis: S. epidermidis* antigens include slime-associated antigen (SAA).

*Clostridium tetani* (Tetanus): Tetanus antigens include tetanus toxoid (TT), may be used as a carrier protein in conjunction/conjugated with the compositions of the present disclosure.

*Corynebacterium diphtheriae* (Diphtheria): Diphtheria antigens include diphtheria toxin, including detoxified, such as $CRM_{197}$. Additionally, antigens capable of modulating, inhibiting or associated with ADP ribosylation are contemplated for combination/co-administration/conjugation with the compositions of the present disclosure. The diphtheria toxoids may be used as carrier proteins.

*Haemophilus influenzae* B (Hib): Hib antigens include a Hib saccharide antigen.

*Pseudomonas aeruginosa:* Pseudomonas antigens include endotoxin A, Wzz protein, *P. aeruginosa* LPS, more particularly LPS isolated from PAO1 (O5 serotype), and/or Outer Membrane Proteins, including Outer Membrane Proteins F (OprF).

*Legionella pneumophila.* Bacterial antigens may be derived from *Legionella pneumophila.*

*Streptococcus agalactiae* (Group B *Streptococcus*): Group B *Streptococcus* antigens include a protein or saccharide antigen identified in WO 02/34771, WO 03/093306, WO 04/041157, or WO 2005/002619 (including proteins GBS 80, GBS 104, GBS 276 and GBS 322, and including saccharide antigens derived from serotypes Ia, Ib, Ia/c, II, III, IV, V, VI, VII and VIII).

*Neisseria gonorrhoeae:* Gonorrhoeae antigens include Por (or porin) protein, such as PorB, a transferring binding protein, such as TbpA and TbpB, a opacity protein (such as Opa), a reduction-modifiable protein (Rmp), and outer membrane vesicle (OMV) preparations (see e.g., WO99/24578, WO99/36544, WO99/57280, WO02/079243).

*Chlamydia trachomatis: Chlamydia trachomatis* antigens include antigens derived from serotypes A, B, Ba and C (agents of trachoma, a cause of blindness), serotypes $L_1$, $L_2$ & $L_3$ (associated with Lymphogranuloma venereum), and serotypes, D-K. *Chlamydia* trachomas antigens may also include an antigen identified in WO 00/37494, WO 03/049762, WO 03/068811, or WO 05/002619, including PepA (CT045), LcrE (CT089), ArtJ (CT381), DnaK (CT396), CT398, OmpH-like (CT242), L7/L12 (CT316), OmcA (CT444), AtosS (CT467), CT547, Eno (CT587), HrtA (CT823), and MurG (CT761).

*Treponema pallidum* (Syphilis): Syphilis antigens include TmpA antigen.

*Haemophilus ducreyi* (causing chancroid): Ducreyi antigens include outer membrane protein (DsrA).

*Enterococcus faecalis* or *Enterococcus faecium*: Antigens include a trisaccharide repeat or other *Enterococcus* derived antigens provided in U.S. Pat. No. 6,756,361.

*Helicobacter pylori*: *H. pylori* antigens include Cag, Vac, Nap, HopX, HopY and/or urease antigen.

*Staphylococcus saprophyticus*: Antigens include the 160 kDa hemagglutinin of *S. saprophyticus* antigen.

*Yersinia enterocolitica* Antigens include LPS.

*E. coli*: *E. coli* antigens may be derived from enterotoxigenic *E. coli* (ETEC), enteroaggregative *E. coli* (EAggEC), diffusely adhering *E. coli* (DAEC), enteropathogenic *E. coli* (EPEC), and/or enterohemorrhagic *E. coli* (EHEC).

*Bacillus anthracis* (anthrax): *B. anthracis* antigens are optionally detoxified and may be selected from A-components (lethal factor (LF) and edema factor (EF)), both of which may share a common B-component known as protective antigen (PA).

*Yersinia pestis* (plague): Plague antigens include F1 capsular antigen.

*Mycobacterium tuberculosis*: Tuberculosis antigens include lipoproteins, LPS, BCG antigens, a fusion protein of antigen 85B (Ag85B) and/or ESAT-6 optionally formulated in cationic lipid vesicles, *Mycobacterium tuberculosis* (Mtb) isocitrate dehydrogenase associated antigens, and/or MPT51 antigens.

*Rickettsia*: Antigens include outer membrane proteins, including the outer membrane protein A and/or B (OmpB).

*Listeria monocytogenes.* Bacterial antigens may be derived from *Listeria monocytogenes.*

*Chlamydia pneumoniae*: Antigens include those identified in WO 02/02606.

*Vibrio cholerae*: Antigens include proteinase antigens, LPS, particularly lipopolysaccharides of *Vibrio cholerae* II, 01 Inaba 0-specific polysaccharides, *V. cholera* 0139, antigens of IEM108 vaccine, and/or Zonula occludens toxin (Zot).

*Salmonella typhi* (typhoid fever): Antigens include capsular polysaccharides, including conjugates (Vi, i.e., vax-TyVi).

*Borrelia burgdorferi* (Lyme disease): Antigens include lipoproteins (such as OspA, OspB, Osp C and Osp D), other surface proteins such as OspE-related proteins (Erps), decorin-binding proteins (such as DbpA), and antigenically variable VI proteins, such as antigens associated with P39 and P13 VlsE Antigenic Variation Protein.

*Porphyromonas gingivalis*: Antigens include *P. gingivalis* outer membrane protein (OMP).

*Klebsiella*: Antigens include an OMP, including OMP A, or a polysaccharide optionally conjugated to tetanus toxoid.

Further bacterial antigens of the instant disclosure may be capsular antigens, polysaccharide antigens or protein antigens of any of the above. Further bacterial antigens may also include an outer membrane vesicle (OMV) preparation. Additionally, antigens include live, attenuated, and/or purified versions of any of the aforementioned bacteria. The antigens of the present disclosure may be derived from gram-negative or gram-positive bacteria. The antigens of the present disclosure may be derived from aerobic or anaerobic bacteria.

Additionally, any of the above bacterial-derived saccharides (polysaccharides, LPS, LOS or oligosaccharides) may be conjugated to another agent or antigen, such as a carrier protein (for example $CRM_{197}$). Such conjugation may be direct conjugation effected by reductive amination of carbonyl moieties on the saccharide to amino groups on the protein, as provided in U.S. Pat. No. 5,360,897. Alternatively, the saccharides may be conjugated through a linker, such as, with succinamide or other linkages.

Viral Antigens

Viral antigens suitable for use in the compositions as disclosed include purified subunit formulations, viral proteins which may be isolated, purified or derived from a virus, and Virus Like Particles (VLPs). Viral antigens may be derived from viruses propagated on cell culture or other substrate. Alternatively, viral antigens may be expressed recombinantly. Viral antigens include epitopes which are exposed on the surface of the virus during at least one stage of its life cycle. Viral antigens may be conserved across multiple serotypes or isolates. Viral antigens include antigens derived from one or more of the viruses set forth below as well as the specific antigens examples identified below.

Orthomyxovirus: Viral antigens may be derived from an Orthomyxovirus, such as *Influenza* A, B and C. Orthomyxovirus antigens may be selected from one or more of the viral proteins, including hemagglutinin (HA), neuraminidase (NA), nucleoprotein (NP), matrix protein (M1), membrane protein (M2), one or more of the transcriptase components (PB1, PB2 and PA). In embodiments, antigens include HA and NA.

Influenza antigens may be derived from interpandemic (annual) flu strains. Alternatively, influenza antigens may be derived from strains with the potential to cause pandemic a pandemic outbreak (i.e., influenza strains with new haemagglutinin compared to the haemagglutinin in currently circulating strains, or influenza strains which are pathogenic in avian subjects and have the potential to be transmitted horizontally in the human population, or influenza strains which are pathogenic to humans).

Paramyxoviridae viruses: Viral antigens may be derived from Paramyxoviridae viruses, such as Pneumoviruses (RSV), Paramyxoviruses (PIV) and Morbilliviruses (Measles).

Pneumovirus: Viral antigens may be derived from a Pneumovirus, such as Respiratory syncytial virus (RSV), Bovine respiratory syncytial virus, Pneumonia virus of mice, and Turkey rhinotracheitis virus. In embodiments, the Pneumovirus is RSV. Pneumovirus antigens may be selected from one or more of the following proteins, including surface proteins Fusion (F), Glycoprotein (G) and Small Hydrophobic protein (SH), matrix proteins M and M2, nucleocapsid proteins N, P and L and nonstructural proteins NS1 and NS2. Pneumovirus antigens may include F, G and M. Pneumovirus antigens may also be formulated in or derived from chimeric viruses. For example, chimeric RSV/PIV viruses may comprise components of both RSV and PIV Paramyxovirus: Viral antigens may be derived from a Paramyxovirus, such as Parainfluenza virus types 1-4 (PIV), Mumps, Sendai viruses, Simian virus 5, Bovine parainfluenza virus and Newcastle disease virus. In embodiments, the Paramyxovirus is PIV or Mumps. Paramyxovirus antigens may be selected from one or more of the following proteins: Hemagglutinin-Neuraminidase (HN), Fusion proteins F1 and F2, Nucleoprotein (NP), Phosphoprotein (P), Large protein (L), and Matrix protein (M). Paramyxovirus proteins may include HN, F1 and F2. Paramyxovirus antigens may also be formulated in or derived from chimeric viruses. For example, chimeric RSV/PIV viruses may comprise components of both RSV and PIV. Commercially available mumps vaccines include live attenuated mumps virus, in either a monovalent form or in combination with measles and rubella vaccines (MMR).

Morbillivirus: Viral antigens may be derived from a Morbillivirus, such as Measles. Morbillivirus antigens may be selected from one or more of the following proteins: hemagglutinin (H), Glycoprotein (G), Fusion factor (F), Large protein (L), Nucleoprotein (NP), Polymerase phosphoprotein (P), and Matrix (M). Commercially available measles vaccines include live attenuated measles virus, typically in combination with mumps and rubella (MMR).

Picornavirus: Viral antigens may be derived from Picornaviruses, such as Enteroviruses, Rhinoviruses, Heparnavirus, Cardioviruses and Aphthoviruses. Antigens derived from Enteroviruses, such as Poliovirus are may be used.

Enterovirus: Viral antigens may be derived from an Enterovirus, such as Poliovirus types 1, 2 or 3, Coxsackie A virus types 1 to 22 and 24, Coxsackie B virus types 1 to 6, Echovirus (ECHO) virus) types 1 to 9, 11 to 27 and 29 to 34 and Enterovirus 68 to 71. In embodiments, the Enterovirus may be poliovirus. Enterovirus antigens may include one or more of the following Capsid proteins VP1, VP2, VP3 and VP4. Commercially available polio vaccines include Inactivated Polio Vaccine (IPV) and Oral poliovirus vaccine (OPV).

Heparnavirus: Viral antigens may be derived from an Heparnavirus, such as Hepatitis A virus (HAV). Commercially available HAV vaccines include inactivated HAV vaccine.

Togavirus: Viral antigens may be derived from a Togavirus, such as a Rubivirus, an Alphavirus, or an Arterivirus. Antigens derived from Rubivirus, such as Rubella virus, may be used. Togavirus antigens may be selected from E1, E2, E3, C, NSP-1, NSPO-2, NSP-3 or NSP-4. Togavirus antigens include E1, E2 or E3. Commercially available Rubella vaccines include a live cold-adapted virus, typically in combination with mumps and measles vaccines (MMR).

Flavivirus: Viral antigens may be derived from a Flavivirus, such as Tick-borne encephalitis (TBE), Dengue (types 1, 2, 3 or 4), Yellow Fever, Japanese encephalitis, West Nile encephalitis, St. Louis encephalitis, Russian spring-summer encephalitis, Powassan encephalitis. Flavivirus antigens may be selected from PrM, M, C, E, NS-1, NS-2a, NS2b, NS3, NS4a, NS4b, and NS5. Flavivirus antigens may include PrM, M and E. Commercially available TBE vaccine include inactivated virus vaccines.

Pestivirus: Viral antigens may be derived from a Pestivirus, such as Bovine viral diarrhea (BVDV), Classical swine fever (CSFV) or Border disease (BDV).

Hepadnavirus: Viral antigens may be derived from a Hepadnavirus, such as Hepatitis B virus. Hepadnavirus antigens may be selected from surface antigens (L, M and S), core antigens (HBc, HBe). Commercially available HBV vaccines include subunit vaccines comprising the surface antigen S protein.

Hepatitis C virus: Viral antigens may be derived from a Hepatitis C virus (HCV). HCV antigens may be selected from one or more of E1, E2, E1/E2, NS345 polyprotein, NS 345-core polyprotein, core, and/or peptides from the nonstructural regions.

Rhabdovirus: Viral antigens may be derived from a Rhabdovirus, such as a Lyssavirus (Rabies virus) and Vesiculovirus (VSV). Rhabdovirus antigens may be selected from glycoprotein (G), nucleoprotein (N), large protein (L), nonstructural proteins (NS). Commercially available Rabies virus vaccine comprise killed virus grown on human diploid cells or fetal rhesus lung cells.

Caliciviridae; Viral antigens may be derived from Caliciviridae, such as Norwalk virus, and Norwalk-like Viruses, such as Hawaii Virus and Snow Mountain Virus.

Coronavirus: Viral antigens may be derived from a Coronavirus, SARS, Human respiratory coronavirus, Avian infectious bronchitis (IBV), Mouse hepatitis virus (MHV), and Porcine transmissible gastroenteritis virus (TGEV). Coronavirus antigens may be selected from spike (S), envelope (E), matrix (M), nucleocapsid (N), and Hemagglutinin-esterase glycoprotein (HE). In embodiments, the Coronavirus antigen is derived from a SARS virus. SARS viral antigens are described in WO 04/92360;

Retrovirus: Viral antigens may be derived from a Retrovirus, such as an Oncovirus, a Lentivirus or a Spumavirus. Oncovirus antigens may be derived from HTLV-1, HTLV-2 or HTLV-5. Lentivirus antigens may be derived from HIV-1 or HIV-2. Retrovirus antigens may be selected from gag, pol, env, tax, tat, rex, rev, nef, vif, vpu, and vpr. HIV antigens may be selected from gag (p24gag and p55gag), env (gp160 and gp41), pol, tat, nef, rev vpu, miniproteins, (e.g., p55 gag and gp140v delete). HIV antigens may be derived from one or more of the following strains: $HIV_{111b}$, $HIV_{sF2}$, $HIV_{LAV}$, $HIV_{LAI}$, $HIV_{MN}$, $HIV\text{-}1_{CM235}$, $HIV\text{-}1_{us4}$.

Reovirus: Viral antigens may be derived from a Reovirus, such as an Orthoreovirus, a Rotavirus, an Orbivirus, or a Coltivirus. Reovirus antigens may be selected from structural proteins λ1, λ 2, λ3, μ1, μ2, σ1, σ2, or σ3, or nonstructural proteins σNS, μNS, or σ1s. Reovirus antigens may be derived from a Rotavirus. Rotavirus antigens may be selected from VP1, VP2, VP3, VP4 (or the cleaved product VP5 and VP8), NSP 1, VP6, NSP3, NSP2, VP7, NSP4, or NSP5. Rotavirus antigens may include VP4 (or the cleaved product VP5 and VP8), and VP7. See, e.g., WO 2005/021033, WO 2003/072716, WO 2002/11540, WO 2001/12797, WO 01/08495, WO 00/26380, WO 02/036172; herein incorporated by reference in their entireties.

Parvovirus: Viral antigens may be derived from a Parvovirus, such as Parvovirus B19. Parvovirus antigens may be selected from VP-1, VP-2, VP-3, NS-1 and NS-2. In embodiments, the Parvovirus antigen is capsid protein VP-2.

Delta hepatitis virus (HDV): Viral antigens may be derived HDV, particularly .delta.-antigen from HDV (see, e.g., U.S. Pat. No. 5,378,814).

Hepatitis E virus (HEV): Viral antigens may be derived from HEV.

Hepatitis G virus (HGV): Viral antigens may be derived from HGV

Human Herpesvirus: Viral antigens may be derived from a Human Herpesvirus, such as Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8). Human Herpesvirus antigens may be selected from immediate early proteins (α), early proteins (β), and late proteins (γ). HSV antigens may be derived from HSV-1 or HSV-2 strains. HSV antigens may be selected from glycoproteins gB, gC, gD and gH, fusion protein (gB), or immune escape proteins (gC, gE, or gI). VZV antigens may be selected from core, nucleocapsid, tegument, or envelope proteins. Alive attenuated VZV vaccine is commercially available. EBV antigens may be selected from early antigen (EA) proteins, viral capsid antigen (VCA), and glycoproteins of the membrane antigen (MA). CMV antigens may be selected from capsid proteins, envelope glycoproteins (such as gB and gH), and tegument proteins Papovaviruses: Antigens may be derived from Papovaviruses, such as Papillomaviruses and Polyomaviruses. Papillomaviruses include HPV serotypes 1, 2, 4, 5, 6, 8, 11, 13, 16, 18, 31, 33, 35, 39, 41, 42, 47, 51, 57, 58, 63 and 65. In embodiments, HPV antigens are derived from serotypes 6, 11, 16 or 18. HPV antigens may include capsid proteins (L1) and (L2), or E1-E7, or fusions thereof. Polyomyavirus viruses include BK virus and JK virus. Polyomavirus antigens may be selected from VP1, VP2 or VP3.

Circovirus: Antigens may be derived from Circoviruses, such as Porcine circovirus (PCV) 1, PCV 2, PCV 3, and PCV 4.

Fungal Antigens

Suitable fungal antigens may be derived from one or more of the fungi set forth below.

Fungal antigens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album,* var. *discoides,* var. *ochraceum, Trichophyton violaceum,* and/or *Trichophyton faviforme.*

Fungal pathogens may be derived from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiosperum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp., *Mucor* spp., *Absidia* spp., *Mortierella* spp., *Cunninghamella* spp., *Saksenaea* spp., *Alternaria* spp., *Curvularia* spp., *Helminthosporium* spp., *Fusarium* spp., *Aspergillus* spp., *Penicillium* spp., *Monolinia* spp., *Rhizoctonia* spp., *Paecilomyces* spp., *Pithomyces* spp., and *Cladosporium* spp.

Processes for producing a fungal antigens are well known in the art (see U.S. Pat. No. 6,333,164). In one method, a solubilized fraction extracted and separated from an insoluble fraction obtainable from fungal cells of which cell wall has been substantially removed or at least partially removed, characterized in that the process comprises the steps of: obtaining living fungal cells; obtaining fungal cells of which cell wall has been substantially removed or at least partially removed; bursting the fungal cells of which cell wall has been substantially removed or at least partially removed; obtaining an insoluble fraction; and extracting and separating a solubilized fraction from the insoluble fraction.

Respiratory Antigens

The compositions of the as disclosed herein may include one or more antigens derived from a pathogen which causes respiratory disease. For example, respiratory antigens may be derived from a respiratory virus such as Orthomyxoviruses (influenza), Pneumovirus (RSV), Paramyxovirus (PIV), Morbillivirus (measles), Togavirus (Rubella), VZV, and Coronavirus (SARS). Respiratory antigens may be derived from a bacteria which causes respiratory disease, such as *Streptococcus pneumoniae, Pseudomonas aeruginosa, Bordetella pertussis, Mycobacterium tuberculosis, Mycoplasma pneumoniae, Chlamydia pneumoniae, Bacillus anthracis,* and *Moraxella catarrhalis.* Examples of specific antigens derived from these pathogens are described above.

The immunogenic compositions as disclosed herein may be prepared in various forms. For example, the compositions may be prepared as injectables, either as liquid solutions or suspensions. Solid forms suitable for solution in, or suspension in, liquid vehicles prior to injection may also be prepared (e.g., a lyophilized composition or a spray-freeze dried composition). The composition may be prepared for topical administration e.g., as an ointment, cream or powder. The composition may be prepared for oral administration e.g., as a tablet or capsule or as a spray. The composition may be prepared for pulmonary administration e.g., as an inhaler, using a fine powder or a spray. The composition may be prepared as a suppository or pessary. The composition may be prepared for nasal, aural or ocular administration e.g., as drops. Preparation of such pharmaceutical compositions is within the general skill of the art. See, e.g., Remington's Pharmaceutical Sciences, Mack Publishing Company, Easton, Pa., 18th edition, 1990.

The composition may be in kit form, designed such that a combined composition is reconstituted just prior to administration to a patient. Such kits may comprise one or more Sapovirus antigens or nucleic acids encoding such antigens in liquid form, and any of the additional antigens and adjuvants as described herein.

Immunogenic compositions comprising polypeptide antigens as disclosed are vaccine compositions. The pH of such compositions is between 6 and 8, about 7. The pH may be maintained by the use of a buffer. The composition may be sterile and/or pyrogen-free. The composition may be isotonic with respect to the subject. Vaccines according to the instant disclosure may be used either prophylactically or therapeutically, but will typically be prophylactic and may be used to treat animals (including farm, game, companion and laboratory mammals).

Immunogenic compositions used as vaccines comprise an immunologically effective amount of antigen(s) and/or nucleic acids encoding antigen(s), as well as any other components, as needed. By "immunologically effective amount," it is meant that the administration of that amount to an individual, either in a single dose or as part of a series, is effective for treatment or prevention. This amount varies depending upon the health and physical condition of the individual to be treated, age, the taxonomic group of individual to be treated (e.g., swine, cattle, and the like), the capacity of the individual's immune system to synthesize antibodies, the degree of protection desired, the formulation of the vaccine, the treating veterinarian's assessment of the medical situation, and other relevant factors. It is expected that the amount will fall in a relatively broad range that may be determined through routine trials.

Administration

Compositions of as disclosed herein will generally be administered directly to a subject. Direct delivery may be accomplished by parenteral injection (e.g., subcutaneously, intraperitoneally, intravenously, intramuscularly, or to the interstitial space of a tissue), or mucosally, such as by rectal, oral (e.g., tablet, spray), vaginal, topical, transdermal (see, e.g., WO99/27961) or transcutaneous (see e.g., WO02/074244 and WO02/064162), intranasal (see, e.g., WO03/028760), ocular, aural, pulmonary or other mucosal administration. Immunogenic compositions may also be administered topically by direct transfer to the surface of the skin. Topical administration may be accomplished without utilizing any devices, or by contacting naked skin with the immunogenic composition utilizing a bandage or a bandage-like device (see, e.g., U.S. Pat. No. 6,348,450).

In embodiments, the mode of administration may be parenteral, mucosal or a combination of mucosal and parenteral immunizations. In one aspect, the mode of administration is parenteral, mucosal or a combination of mucosal and parenteral immunizations in a total of 1-2 vaccinations 1-3 weeks apart. In one aspect, the route of administration includes but is not limited to oral delivery, intra-muscular delivery and a combination of oral and intra-muscular delivery.

It has already been demonstrated that mucosal and systemic immune responses to antigens, such as *Helicobacter pylori* antigens may be enhanced through mucosal priming followed by systemic boosting immunizations. In embodiments, the method for treating an infection by a Sapovirus, comprises mucosally administering to a subject in need thereof a first immunogenic composition comprising one or more Sapovirus antigens followed by parenterally administering a therapeutically effective amount of a second immunogenic composition comprising one or more Sapovirus antigens.

The immunogenic composition may be used to elicit systemic and/or mucosal immunity, to elicit an enhanced systemic and/or mucosal immunity.

In embodiments, the immune response is characterized by the induction of a serum IgG and/or intestinal IgA immune response.

As noted above, prime-boost methods may be employed where one or more gene delivery vectors and/or polypeptide antigens are delivered in a "priming" step and, subsequently, one or more second gene delivery vectors and/or polypeptide antigens are delivered in a "boosting" step. In certain embodiments, priming and boosting with one or more gene delivery vectors or polypeptide antigens described herein is followed by additional boosting with one or more polypeptide-containing compositions (e.g., polypeptides comprising Sapovirus antigens).

In any method involving co-administration, the various compositions may be delivered in any order. Thus, in embodiments including delivery of multiple different compositions or molecules, the nucleic acids need not be all delivered before the polypeptides. For example, the priming step may include delivery of one or more polypeptides and the boosting comprises delivery of one or more nucleic acids and/or one or more polypeptides. Multiple polypeptide administrations may be followed by multiple nucleic acid administrations or polypeptide and nucleic acid administrations may be performed in any order. Thus, one or more of the gene delivery vectors described herein and one or more of the polypeptides described herein may be co-administered in any order and via any administration route. Therefore, any combination of polynucleotides and polypeptides described herein may be used to elicit an immune reaction.

Dosage Regime

Dosage treatment may be according to a single dose schedule or a multiple dose schedule. Multiple doses may be used in a primary immunization schedule and/or in a booster immunization schedule. In a multiple dose schedule, the various doses may be given by the same or different routes, e.g., a parenteral prime and mucosal boost, a mucosal prime and parenteral boost, and the like.

In embodiments, the dosage regime enhances the avidity of the antibody response leading to antibodies with a neutralizing characteristic. An in-vitro neutralization assay may be used to test for neutralizing antibodies.

There is a strong case for a correlation between serum antibody levels and protection from disease caused by Sapovirus.

Tests to Determine the Efficacy of an Immune Response

One way of assessing efficacy of therapeutic treatment involves monitoring infection after administration of a composition of the as disclosed. One way of assessing efficacy of prophylactic treatment involves monitoring immune responses against the antigens in the compositions of the as disclosed after administration of the composition.

Another way of assessing the immunogenicity of the component proteins of the immunogenic compositions of the present disclosure is to express the proteins recombinantly and to screen patient sera or mucosal secretions by immunoblot. A positive reaction between the protein and the patient serum indicates that the patient has previously mounted an immune response to the protein in question—that is, the protein is an immunogen. This method may also be used to identify immunodominant proteins and/

Another way of checking efficacy of therapeutic treatment involves monitoring infection after administration of the compositions of the present disclosure. One way of checking efficacy of prophylactic treatment involves monitoring immune responses both systemically (such as monitoring the level of IgG1 and IgG2a production) and mucosally (such as monitoring the level of IgA production) against the antigens in the compositions of the present disclosure after administration of the composition. Typically, serum specific antibody responses are determined post-immunization but pre-challenge whereas mucosal specific antibody body responses are determined post-immunization and post-challenge.

The immunogenic compositions of the present disclosure may be evaluated in in vitro and in vivo animal models prior to host. Particularly useful mouse models include those in which intraperitoneal immunization is followed by either intraperitoneal challenge or intranasal challenge.

The efficacy of immunogenic compositions of the present disclosure may also be determined in vivo by challenging animal models of infection, e.g., guinea pigs or mice or rhesus macaques, with the immunogenic compositions. The immunogenic compositions may or may not be derived from the same strains as the challenge strains. In embodiments, the immunogenic compositions may be derivable from the same strains as the challenge strains.

In vivo efficacy models include but are not limited to: (i) A murine infection model using human strains; (ii) a murine disease model which is a murine model using a mouse-adapted strain, such as strains which are particularly virulent in mice and (iii) a primate model using human isolates. A human challenge model, which is supported by the NIH and Center for Disease Control (CDC) is also available.

The immune response may be one or both of a TH1 immune response and a TH2 response. The immune response may be an improved or an enhanced or an altered immune response. The immune response may be one or both of a systemic and a mucosal immune response. In embodiments, the immune response is an enhanced systemic and/or mucosal response.

An enhanced systemic and/or mucosal immunity is reflected in an enhanced TH1 and/or TH2 immune response. In embodiments, the enhanced immune response includes an increase in the production of IgG1 and/or IgG2a and/or IgA. In embodiments, the mucosal immune response is a TH2 immune response. In one aspect, the mucosal immune response includes an increase in the production of IgA.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. In embodiments, the enhanced TH2 immune response will include an increase in IgG1 production.

A TH1 immune response may include one or more of an increase in CTLs, an increase in one or more of the cytokines associated with a TH 1 immune response (such as IL-2, IFNγ, and TNFβ), an increase in activated macrophages, an increase in NK activity, or an increase in the production of IgG2a. In embodiments, the enhanced TH1 immune response will include an increase in IgG2a production.

Immunogenic compositions of the present disclosure, in particular, immunogenic composition comprising one or more antigens of the present disclosure may be used either alone or in combination with other antigens optionally with an immunoregulatory agent capable of eliciting a Th1 and/or Th2 response.

The immunogenic composition of the present disclosure may also comprise one or more immunoregulatory agents, such as a mineral salt, such as an aluminum salt and an oligonucleotide containing a CpG motif. In embodiments, the immunogenic composition includes both an aluminum salt and an oligonucleotide containing a CpG motif. Alternatively, the immunogenic composition includes an ADP ribosylating toxin, such as a detoxified ADP ribosylating toxin and an oligonucleotide containing a CpG motif. In one aspect, the one or more immunoregulatory agents include an adjuvant. The adjuvant may be selected from one or more of the group consisting of a TH1 adjuvant and TH2 adjuvant, further discussed above.

The immunogenic compositions of the present composition may elicit both a cell mediated immune response as well as a humoral immune response in order to effectively address an infection. This immune response may induce long lasting (e.g., neutralizing) antibodies and a cell mediated immunity that may quickly respond upon exposure to one or more infectious antigens. By way of example, evidence of neutralizing antibodies in a subject's blood samples is considered as a surrogate parameter for protection since their formation is of decisive importance for virus elimination in TBE infections.

Use of the Immunogenic Compositions as Medicaments

The instant disclosure also provides a composition for use as a medicament. The medicament may be able to raise an immune response in a mammal (i.e., it is an immunogenic composition) and may be a vaccine. The present disclosure also provides the use of the instant compositions in the manufacture of a medicament for raising an immune response in a mammal. The medicament may be a vaccine. In embodiments, the vaccine is used to prevent and/or treat an intestinal infection such as gastroenteritis, including acute gastroenteritis. The gastroenteritis may result from an imbalance in ion and/or water transfer resulting in both watery diarrhea and/or intestinal peristalisis and/or motility (vomiting).

The instant disclosure provides methods for inducing or increasing an immune response using the compositions described above. The immune response may be protective and may induce antibodies and/or cell-mediated immunity (including systemic and mucosal immunity). Immune responses include booster responses.

The present disclosure also provides a method for raising an immune response in a mammal comprising the step of administering an effective amount of a composition of the instant disclosure. The immune response may be protective and may involve antibodies and/or cell-mediated immunity. In embodiments, the immune response includes one or both of a TH1 immune response and a TH2 immune response. The method may raise a booster response.

Kits

The present disclosure also provides kits comprising one or more containers of compositions as described herein. Compositions may be in liquid form or may be lyophilized, as may individual antigens. Suitable containers for the compositions include, for example, bottles, vials, syringes, and test tubes. Containers may be formed from a variety of materials, including glass or plastic. A container may have a sterile access port (for example, the container may be an intravenous solution bag or a vial having a stopper pierceable by a hypodermic injection needle).

The kit may further comprise a second container comprising a pharmaceutically-acceptable buffer, such as phosphate-buffered saline, Ringer's solution, or dextrose solution. It may also contain other materials useful to the end-user, including other pharmaceutically acceptable formulating solutions such as buffers, diluents, filters, needles, and syringes or other delivery device. The kit may further include a third component comprising an adjuvant.

The kit may also comprise a package insert containing written instructions for methods of inducing immunity or for treating infections. The package insert may be an unapproved draft package insert or may be a package insert approved by the Food and Drug Administration (FDA) or other regulatory body.

In embodiments, a delivery device is pre-filled with the immunogenic compositions as disclosed herein.

Methods of Producing Sapovirus-Specific Antibodies

The Sapovirus polypeptides described herein may be used to produce Sapovirus-specific polyclonal and monoclonal antibodies that specifically bind to/are selective for Sapovirus antigens, respectively. Polyclonal antibodies may be produced by administering a Sapovirus polypeptide to a mammal, such as a mouse, a rabbit, a goat, or a horse. Serum from the immunized animal is collected and the antibodies are purified from the plasma by, for example, precipitation with ammonium sulfate, followed by chromatography, including affinity chromatography. Techniques for producing and processing polyclonal antisera are known in the art.

Monoclonal antibodies directed against Sapovirus-specific epitopes present in the polypeptides may also be readily produced. Normal B cells from a mammal, such as a mouse, immunized with a Sapovirus polypeptide, may be fused with, for example, HAT-sensitive mouse myeloma cells to produce hybridomas. Hybridomas producing Sapovirus-specific antibodies may be identified using RIA or ELISA and isolated by cloning in semi-solid agar or by limiting dilution. Clones producing Sapovirus-specific antibodies are isolated by another round of screening.

Antibodies, i.e., monoclonal and antibodies from polyclonal sera (polyclonal), which are directed against Sapovirus epitopes, are particularly useful for detecting the presence of Sapovirus antigens in a sample, such as a serum sample from a Sapovirus-infected human. An immunoassay for a Sapovirus antigen may utilize one antibody or several antibodies. An immunoassay for a Sapovirus antigen may use, for example, a monoclonal antibody directed towards a Sapovirus epitope, a combination of monoclonal antibodies directed towards epitopes of one Sapovirus polypeptide, monoclonal antibodies directed towards epitopes of different Sapovirus polypeptides, polyclonal antibodies directed towards the same Sapovirus antigen, polyclonal antibodies directed towards different Sapovirus antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Sapovirus particles or antigens by immunoaffinity columns. The antibodies may be affixed to a solid support by, for example, adsorption or by covalent linkage so that the antibodies retain their immunoselective activity. Optionally, spacer groups may be included so that the antigen binding site of the antibody remains accessible. The immobilized antibodies may then be used to bind Sapovirus particles or antigens from a biological sample, such as blood or plasma. The bound Sapovirus particles or antigens are recovered from the column matrix by, for example, a change in pH.

The antigens recovered may be sequenced, and the sequences used to make constructs for recombinant expression of the recovered antigen by molecular biological means. As used herein, "construct" means an artificially-designed segment of nucleic acid (DNA or RNA) borne on a vector that can be used to incorporate genetic material into a target tissue or cell.

The following examples are intended to illustrate but not limit the invention.

EXAMPLES

The following examples are intended to illustrate but not limit the invention.

Materials and Methods:

40 female Balb/c mice were randomly placed into 10 cages of 4 mice each. Mice were allowed to acclimate. Seven cages of mice (total of 28 mice) were vaccinated subcutaneously with a 0.2 ml dose containing formulated with VRx 19030 (recombinant sapovirus protein; SEQ ID NO:2), serial number PV1070820 after mixing with Emulsigen serial PV0080621. The remaining 3 cages of mice (total of 12 mice) were held as non-vaccinated controls. Vaccinated mice were boostered at Day 21 with the same serials and exsanguinated on Day 35. Whole blood was separated into sera. Sera was kept as individual samples as well as pools generated proportionally for the samples from each of 4 mice contained in a specific cage. These pools were treated as 1 individual sample.

Sera was tested via indirect ELISA in duplicate, where plates were coated with 0.1 µg V19030 (recombinant Sapovirus protein) or V19045 (recombinant IAV-S H3 protein) diluted in carbonate coating buffer. Plates were washed 3× with 1× PBS-T. Antigen plates were then blocked with 1% polyvinyl alcohol diluted in PBS for 1 hour at 37° C. Block was removed. Five-fold serial dilutions starting at 1:1000 were performed of the sera in duplicate. Sera was allowed to incubate for 1 hour at 37° C. Plates were washed 3× with 1× PBS-T. Goat-anti-mouse IgG (H+L) horseradish peroxidase (HRP) conjugate was diluted 1:10000 (Table 1) or 1:17.5000 (Table 2), added to plates and allowed to incubate for 1 hour at 37° C. Plates were washed 3× with 1× PBS-T. TMB (3,3',5,5'-Tetramethylbenzidine) substrate was added to plates and allowed to incubate at RT (room temperature) for 3 minutes (Table 1) or 6.5 minutes (Table 2). Plates were stopped with 1N $H_2SO_4$ (sulfuric acid) and read for OD at 450 nm. Controls were performed utilizing non-vaccinated mice, as well as 1° antibody only, 2° Antibody only, and coating antigen only. Duplicate wells were averaged.

TABLE 1

(Comparison of Vaccinate vs. Non-Vaccinate Response on Homologous vs. Heterologous Coating Antigen).

| | Homologous Coating Antigen (recombinantly expressed Sapovirus) | | Heterologous Coating Antigen (recombinantly expressed IAV-S) | |
|---|---|---|---|---|
| 1° Ab Dilution | Vaccinate Pool (Avg OD) | Non-Vaccinate Pool (Avg OD) | Vaccinate Pool (Avg OD) | Non-Vaccinate Pool (Avg OD) |
| 1:1000 | 1.70 | 0.13 | 0.59 | 0.08 |
| 1:5000 | 1.24 | 0.10 | 0.37 | 0.07 |
| 1:25000 | 0.55 | 0.08 | 0.16 | 0.06 |
| 1:125000 | 0.19 | 0.08 | 0.08 | 0.06 |
| 1:625000 | 0.11 | 0.08 | 0.06 | 0.07 |
| 1:3125000 | 0.09 | 0.08 | 0.06 | 0.07 |
| 1:15625000 | 0.11 | 0.09 | 0.07 | 0.07 |

| | Coating Ag + 1° + 2° OD | Coating Ag + 1° OD | Coating Ag + 2° OD | Coating Ag Only OD |
| Homologous Coating Antigen (recombinantly expressed Sapovirus | 0.17 | 0.05 | 0.10 | 0.05 |
| Heterologous Coating Antigen (recombinantly expressed IAV-S) | 0.10 | 0.04 | 0.07 | 0.04 |

TABLE 2

(Immune Response to recombinant Sapovirus protein).

| Sera | Vaccinate Average | Non-Vaccinate Average | Vaccinate (Pool by Cage) | | | | | | | Control (Pool by Cage) | | |
|---|---|---|---|---|---|---|---|---|---|---|---|---|
| Dilution | (OD) | (OD) | 860 | 861 | 862 | 863 | 864 | 865 | 866 | 867 | 868 | 869 |
| 1:1000 | 0.812 | 0.083 | 0.795 | 0.846 | 0.794 | 0.856 | 0.835 | 0.820 | 0.743 | 0.082 | 0.087 | 0.079 |
| 1:5000 | 0.437 | 0.065 | 0.393 | 0.434 | 0.417 | 0.431 | 0.468 | 0.463 | 0.451 | 0.064 | 0.069 | 0.063 |
| 1:25000 | 0.178 | 0.070 | 0.168 | 0.168 | 0.157 | 0.179 | 0.186 | 0.199 | 0.190 | 0.064 | 0.071 | 0.075 |
| 1:125000 | 0.105 | 0.072 | 0.099 | 0.107 | 0.098 | 0.101 | 0.107 | 0.120 | 0.109 | 0.070 | 0.077 | 0.071 |
| 1:625000 | 0.085 | 0.071 | 0.086 | 0.079 | 0.082 | 0.085 | 0.087 | 0.094 | 0.087 | 0.073 | 0.071 | 0.071 |
| 1:3125000 | 0.086 | 0.074 | 0.105 | 0.082 | 0.082 | 0.082 | 0.085 | 0.096 | 0.075 | 0.070 | 0.077 | 0.075 |
| 1:15625000 | 0.088 | 0.089 | 0.095 | 0.086 | 0.082 | 0.085 | 0.088 | 0.098 | 0.082 | 0.094 | 0.089 | 0.083 |

Results:

As may be seen in Tables 1 and 2, vaccinated mice response to the homologous antigen exhibited a higher immunological response as compared to the non-vaccinates. When compared against a heterologous protein generated in the baculovirus platform, the vaccinated mice exhibited a limited response likely due to the baculovirus itself.

Figure 2:
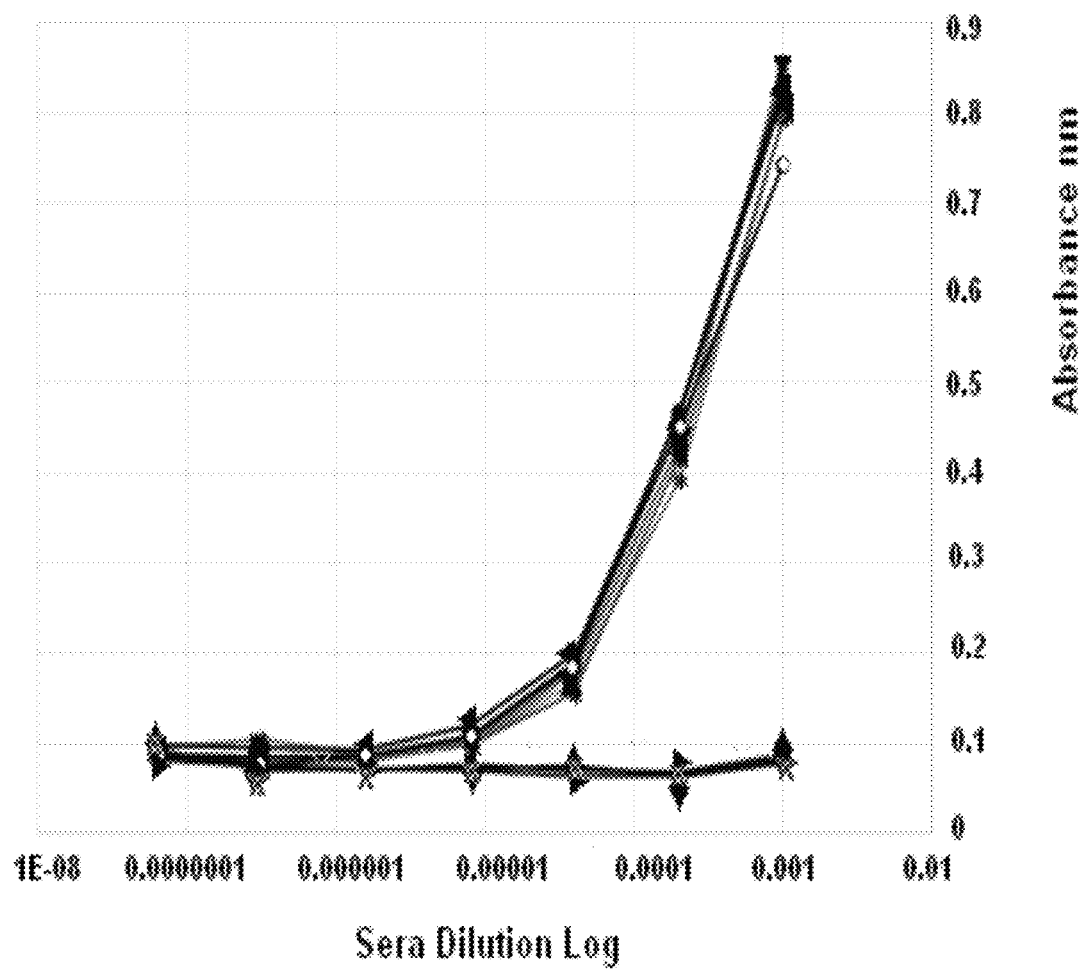

FIG. 1 shows specific immune response to Sapovirus protein. FIG. 2 shows Vaccinate vs Non-Vaccinate response to homologous protein.

All patent literature cited in the instant disclosure is incorporated by reference in their entireties herein.

I claim herein:

1. A method for producing Sapovirus-derived immunogenic polypeptides and/or peptides comprising: culturing a host cell transformed with a nucleic acid under conditions which induce expression of said polypeptides and/or peptides, wherein the polypeptides and/or peptides comprise an amino acid sequence as set forth in the group consisting of SEQ ID NO:2, SEQ ID NO:8, SEQ ID NO:15, SEQ ID NO:21 and combinations thereof, and optionally mixing or co-expressing said immunogenic polypeptides and/or peptides with one or more adjuvants.

2. The method of claim 1, wherein the immunogenic polypeptides and/or peptides comprise a recombinant subunit vaccine, and wherein such expressed polypeptides and/or peptides are generated using baculovirus/insect cell methodology.

3. The method of claim 1, wherein the nucleic acid encoding the Sapovirus derived immunogenic polypeptides and/or peptides is prepared by chemical synthesis.

4. The method of claim 3, wherein the nucleic acid encoding the Sapovirus derived immunogenic polypeptides and/or peptides is generated using a primer-based amplification method.

5. The method of claim 4, wherein the primer-based amplification method is PCR.

6. An immunogenic composition comprising a polypeptide selected from the group consisting of SEQ ID NO: 2, SEQ ID NO:8, SEQ ID NO:15, SEQ ID NO:21 and combinations thereof.

7. A method of eliciting an immunological response in a subject comprising administering a composition as set forth in claim 6.

8. The method of claim 7, further comprising administering an adjuvant.

9. The method of claim 8, wherein administering said immunogenic composition to said subject is via topical, parenteral or mucosal administration.

10. The method of claim 7, wherein said administration is by multiple administrations.

11. The method of claim 10, wherein a first immunogenic composition and at least one second immunogenic composition are the same.

12. The method of claim 10, wherein a first immunogenic composition and the second immunogenic composition are different, and wherein the first immunogenic composition contains a polypeptide comprising the amino acid sequence as set forth in SEQ ID NO:2 and the at least one second immunogenic composition contains a polypeptide comprising an amino acid sequence selected from SEQ ID NO: 8, SEQ ID NO:15 or SEQ ID NO:21.

13. A method for treating an infection by a Sapovirus comprising administering to a subject in need thereof a therapeutically effective amount of an immunogenic composition of claim 6.

14. An isolated recombinant nucleic acid encoding a Sapovirus VP1 protein, wherein the encoding nucleic acid comprises a sequence selected from the group consisting of SEQ ID NO:1, SEQ ID NO:7, SEQ ID NO:14, SEQ ID NO:20, and combinations thereof.

15. A vector comprising the isolated recombinant nucleic acid of claim 14.

16. The vector of claim 15, wherein said vector is a baculovirus vector.

17. An isolated host cell comprising the vector of claim 16.

18. The isolated host cell of claim 17, wherein said isolated host cell is an insect cell.

* * * * *

SEQUENCE LISTING

```
<160> NUMBER OF SEQ ID NOS: 25

<210> SEQ ID NO 1
<211> LENGTH: 1714
<212> TYPE: DNA
<213> ORGANISM: SAPOVIRUS

<400> SEQUENCE: 1
aagcgttact gaattcatgg aggcgcctgc cccaacccgt tcggtggcga gcaacccaga     60
gggtactcaa accagcaatg aatccaggcc agtccagcca gccgggccca tgcccgtggc    120
```

-continued

| | |
|---|---|
| cgcagcccag gcccttgaga tggctgttgc cactggacaa gtcaatgaca ccatccccag | 180 |
| tgtagttaga gaaactttca gcacctacac caatgtcact tggactacac gtcagccagc | 240 |
| aggaaccctg ctcgcccgga tgaccctagg gccaggcctg aatccctaca cactccacct | 300 |
| gtccgccatg tgggccggct ggggagggtc atttgaaatt aaggtggtga tatcggggtc | 360 |
| tggcttgtat gcaggcaaat tgctgtgcgc actcatacca cctggggtag accccagtgc | 420 |
| tgtggaccag cccggggctt ttccccatgc acttgtggat gcgcgcatca ctgagggcgt | 480 |
| caccttcacc cttggggatg tcagggcagt ggattaccac gaaacaggag ctggtgggac | 540 |
| catcgcttgc ttggcactct atgtgtacca accactcatc aaccccttg aaactgcttt | 600 |
| gtcagccgcc atggtgacaa tcgagacccg ccctggccca gactttgggt tcaccctgct | 660 |
| caagcctccc aaccaaacca tggaggcggg acttgatccc agatcgctcc tgccccgcac | 720 |
| ggcaaggaca ctgcggggaa acaggtttgg cagacccatc acagccgtgg tcatagtcgg | 780 |
| catggcacac cagatcaaca ggcacttctc agccgagggc accacgcttg gctggtccac | 840 |
| agccccgatt ggtccttgtg tgggacgcat caattccagg tacaccaaca acggcggcct | 900 |
| cgccgtgctc tcaatgcaac ccctgagcaa tgggcccctt taccccaaca ttatcaacca | 960 |
| ctacccagat gtggctgctt ctaaagcatt caacacaagc actagcctga gtgacaacac | 1020 |
| cacgtgtggt gggggaccta tggtgatctt caatgatgtg ggtgatgtgg ttgagactgt | 1080 |
| gtcctaccaa atgagattta tagcctcaca agccacctcc caaacaccca caatcgttga | 1140 |
| ctacatcaat gcaacatcaa tgggattgtg cagttttggc aactctcggg gggactttgg | 1200 |
| ctcaggccag ctcaatgtgg gcgttgagtt gacctacacc tgtggcacca cagcgatcaa | 1260 |
| tgagaaagtc actacgttca tggatcgcca atacacattt ggtgcacagg ggcccaataa | 1320 |
| tatcatgctc tgggtggaga ctgtactcgg cacgcacacg ggcaacaaca ctgtgtacag | 1380 |
| ctcgcaaccc gacactgtgt ctgccgcact gcagggtcag ccctacaaca taccagatgg | 1440 |
| gtacatggct gtgtggaatg ttaatgcaga cagtgccgat ttccagatag gcctgaggcg | 1500 |
| cgatggcttc tttgtcacca gtggggccat ggcacgcgc atgaccatct cagaggacac | 1560 |
| caccttcacc tacgctggca ttttcacccct caccacccc ctcattggac caagtgggat | 1620 |
| gacaggacgg tcccttcaca gctcacgaaa gggcgaaaac ttgtactttc aaggccatca | 1680 |
| ccatcaccat cactaggcgg ccgcagcatt tact | 1714 |

<210> SEQ ID NO 2
<211> LENGTH: 559
<212> TYPE: PRT
<213> ORGANISM: SAPOVIRUS

<400> SEQUENCE: 2

```
Met Glu Ala Pro Ala Pro Thr Arg Ser Val Ala Ser Asn Pro Glu Gly
1               5                   10                  15

Thr Gln Thr Ser Asn Glu Ser Arg Pro Val Gln Pro Ala Gly Pro Met
            20                  25                  30

Pro Val Ala Ala Ala Gln Ala Leu Glu Met Ala Val Ala Thr Gly Gln
        35                  40                  45

Val Asn Asp Thr Ile Pro Ser Val Val Arg Glu Thr Phe Ser Thr Tyr
    50                  55                  60

Thr Asn Val Thr Trp Thr Thr Arg Gln Pro Ala Gly Thr Leu Leu Ala
65                  70                  75                  80

Arg Met Thr Leu Gly Pro Gly Leu Asn Pro Tyr Thr Leu His Leu Ser
                85                  90                  95
```

```
Ala Met Trp Ala Gly Trp Gly Ser Phe Glu Ile Lys Val Ile
        100                 105                 110

Ser Gly Ser Gly Leu Tyr Ala Gly Lys Leu Leu Cys Ala Leu Ile Pro
        115                 120                 125

Pro Gly Val Asp Pro Ser Ala Val Asp Gln Pro Gly Ala Phe Pro His
    130                 135                 140

Ala Leu Val Asp Ala Arg Ile Thr Glu Gly Val Thr Phe Thr Leu Gly
145                 150                 155                 160

Asp Val Arg Ala Val Asp Tyr His Glu Thr Gly Ala Gly Thr Ile
                165                 170                 175

Ala Cys Leu Ala Leu Tyr Val Tyr Gln Pro Leu Ile Asn Pro Phe Glu
            180                 185                 190

Thr Ala Leu Ser Ala Ala Met Val Thr Ile Glu Thr Arg Pro Gly Pro
                195                 200                 205

Asp Phe Gly Phe Thr Leu Leu Lys Pro Pro Asn Gln Thr Met Glu Ala
        210                 215                 220

Gly Leu Asp Pro Arg Ser Leu Leu Pro Arg Thr Ala Arg Thr Leu Arg
225                 230                 235                 240

Gly Asn Arg Phe Gly Arg Pro Ile Thr Ala Val Val Ile Val Gly Met
                245                 250                 255

Ala His Gln Ile Asn Arg His Phe Ser Ala Glu Gly Thr Thr Leu Gly
            260                 265                 270

Trp Ser Thr Ala Pro Ile Gly Pro Cys Val Gly Arg Ile Asn Ser Arg
        275                 280                 285

Tyr Thr Asn Asn Gly Gly Leu Ala Val Leu Ser Met Gln Pro Leu Ser
        290                 295                 300

Asn Gly Pro Leu Tyr Pro Asn Ile Ile Asn His Tyr Pro Asp Val Ala
305                 310                 315                 320

Ala Ser Lys Ala Phe Asn Thr Ser Thr Ser Leu Ser Asp Asn Thr Thr
                325                 330                 335

Cys Gly Gly Gly Pro Met Val Ile Phe Asn Asp Val Gly Asp Val Val
            340                 345                 350

Glu Thr Val Ser Tyr Gln Met Arg Phe Ile Ala Ser Gln Ala Thr Ser
        355                 360                 365

Gln Thr Pro Thr Ile Val Asp Tyr Ile Asn Ala Thr Ser Met Gly Leu
    370                 375                 380

Cys Ser Phe Gly Asn Ser Arg Gly Asp Phe Gly Ser Gly Gln Leu Asn
385                 390                 395                 400

Val Gly Val Glu Leu Thr Tyr Thr Cys Gly Thr Thr Ala Ile Asn Glu
                405                 410                 415

Lys Val Thr Thr Phe Met Asp Arg Gln Tyr Thr Phe Gly Ala Gln Gly
            420                 425                 430

Pro Asn Asn Ile Met Leu Trp Val Glu Thr Val Leu Gly Thr His Thr
    435                 440                 445

Gly Asn Asn Thr Val Tyr Ser Ser Gln Pro Asp Thr Val Ser Ala Ala
    450                 455                 460

Leu Gln Gly Gln Pro Tyr Asn Ile Pro Asp Gly Tyr Met Ala Val Trp
465                 470                 475                 480

Asn Val Asn Ala Asp Ser Ala Asp Phe Gln Ile Gly Leu Arg Arg Asp
                485                 490                 495

Gly Phe Phe Val Thr Ser Gly Ala Ile Gly Thr Arg Met Thr Ile Ser
            500                 505                 510
```

```
Glu Asp Thr Thr Phe Thr Tyr Ala Gly Ile Phe Thr Leu Thr Thr Pro
            515                 520                 525

Leu Ile Gly Pro Ser Gly Met Thr Gly Arg Ser Leu His Ser Ser Arg
        530                 535                 540

Lys Gly Glu Asn Leu Tyr Phe Gln Gly His His His His His His
545                 550                 555

<210> SEQ ID NO 3
<211> LENGTH: 18
<212> TYPE: DNA
<213> ORGANISM: Artificial Sequence
<220> FEATURE:
<223> OTHER INFORMATION: Foward Primer

<400> SEQUENCE: 3
gtctgcgagc agttgttt                                                     18

<210> SEQ ID NO 4
<211> LENGTH: 21
<212> TYPE: DNA
<213> ORGANISM: Artificial Sequence
<220> FEATURE:
<223> OTHER INFORMATION: Reverse Primer

<400> SEQUENCE: 4
agctcctgtt tcgtggtaat c                                                 21

<210> SEQ ID NO 5
<211> LENGTH: 22
<212> TYPE: DNA
<213> ORGANISM: Artificial Sequence
<220> FEATURE:
<223> OTHER INFORMATION: Forward Primer

<400> SEQUENCE: 5
acaccaatgt cacttggact ac                                                22

<210> SEQ ID NO 6
<211> LENGTH: 20
<212> TYPE: DNA
<213> ORGANISM: Artificial Sequence
<220> FEATURE:
<223> OTHER INFORMATION: Reverse Primer

<400> SEQUENCE: 6
tcaaccacat cacccacatc                                                   20

<210> SEQ ID NO 7
<211> LENGTH: 1712
<212> TYPE: DNA
<213> ORGANISM: SAPOVIRUS

<400> SEQUENCE: 7
accgagctcg aattcatgga ggctcccgcg cctacaagac cagtcgcatc gaatccagaa       60
ggtacacaaa catctaatga aagccgccca gttcaacccg ccggcccgat gcctgtagcg      120
acagcacagg ccctggaaat ggcggtggca acaggtcagg ttaatgacac gatcccgagt      180
gtcgtcagag aaactttcag cacttacaca acgtaacgt ggaccactcg ccagcccgca      240
ggaacgctgt tggcgcgcat gtcgcttggt ccgggtctca acccatacac cttgcacctt      300
tcagcgatgt gggcaggatg gggcggctcc ttcgaaataa aggtaattat ctcgggatcg      360
ggactctacg ccggaaaact cctttgcgcg ctcataccct ccggtgtgga cccgtcggct      420
```

```
gtggatcaac caggtgcctt tcctcacgct ctggtggatg cccgtatcac tgagggcgtg    480
actttcactc tcggagacgt ccgcgctgta gattaccatg aaacaggagc gggcggtact    540
atcgcctgcc ttgcactgta cgtataccaa ccactgatca atccatttga gaccgcgctt    600
tccgctgcta tggtcacgat cgaaacacgt cccggaccgg actttggttt cactcttttg    660
aagcccccta accagacaat ggaagctggt ttggatccac gctctctgct cccgagaaca    720
gcgcgcactc tgagaggaaa caggttcgga agaccgatca ctggcgttgt gatagtcggc    780
atggcccatc agattaatcg tcacttttcg gcacagggaa ccacgcttgg atggtcaact    840 gccccctatag gccatgtgt cggcaggata aattctaagt tcacgaatac aaatggccct    900
gcagtactga gcctgcagcc cctgtctaat ggacctctct atcctaatat tattaatcac    960
tacccagatg tggcggctag tagagctttc aacacgtcta ctagtttggg agcggacacc   1020
acttgcggag gaggaccaat ggttgtgttc aacgacgtgg gcgatgtagt cgagaccgta   1080
tcatatcaga tgagatttat agcgtcccaa gcaacatccc aaaacgccaac gttggtggac   1140 tacatcaacg cgacctcgat ggctgtctgt agctatggca actcacgcgg cgatttcggt   1200
tcgggtcagt tgaatgttgg tgtcgaactc acctatacgt gtggcactac tgctatcaat   1260
gaaaaagtca ctacctttat ggatcgtcag tacaccttcg gtgcccaggg accgaacaac   1320
ataatgctct gggtagaaac ggttcttggt acccacactg caacaacac agtgtacagt   1380 tcacaacctg acacggtatc tgcggccttg caaggccagc cgtataacat ccctgatggc   1440
tacatggcgg tatggaacgt aaatgctgac tctgcagact tccaaatcgg cctccgcagg   1500
gacggtttct tcgttacatc gggcgcaatt ggaactagaa tgacgatctc ggaggacaca   1560
acgtttacat acgccggtat gtttacccctt accacgccgt tgattggacc ttcaggtatg   1620
actggtcgtt cactccattc gagtcaaaag ggcgaaaact tgtactttca aggccatcac   1680
catcaccatc actaggcggc cgcttaatta at                                  1712
```

<210> SEQ ID NO 8
<211> LENGTH: 559
<212> TYPE: PRT
<213> ORGANISM: SAPOVIRUS

<400> SEQUENCE: 8

```
Met Glu Ala Pro Ala Pro Thr Arg Pro Val Ala Ser Asn Pro Glu Gly
1               5                   10                  15

Thr Gln Thr Ser Asn Glu Ser Arg Pro Val Gln Pro Ala Gly Pro Met
            20                  25                  30

Pro Val Ala Thr Ala Gln Ala Leu Glu Met Ala Val Ala Thr Gly Gln
        35                  40                  45

Val Asn Asp Thr Ile Pro Ser Val Val Arg Glu Thr Phe Ser Thr Tyr
    50                  55                  60

Thr Asn Val Thr Trp Thr Thr Arg Gln Pro Ala Gly Thr Leu Leu Ala
65                  70                  75                  80

Arg Met Ser Leu Gly Pro Gly Leu Asn Pro Tyr Thr Leu His Leu Ser
                85                  90                  95

Ala Met Trp Ala Gly Trp Gly Gly Ser Phe Glu Ile Lys Val Ile Ile
            100                 105                 110

Ser Gly Ser Gly Leu Tyr Ala Gly Lys Leu Leu Cys Ala Leu Ile Pro
        115                 120                 125

Pro Gly Val Asp Pro Ser Ala Val Asp Gln Pro Gly Ala Phe Pro His
    130                 135                 140
```

```
Ala Leu Val Asp Ala Arg Ile Thr Glu Gly Val Thr Phe Thr Leu Gly
145                 150                 155                 160

Asp Val Arg Ala Val Asp Tyr His Glu Thr Gly Ala Gly Gly Thr Ile
                165                 170                 175

Ala Cys Leu Ala Leu Tyr Val Tyr Gln Pro Leu Ile Asn Pro Phe Glu
                180                 185                 190

Thr Ala Leu Ser Ala Ala Met Val Thr Ile Glu Thr Arg Pro Gly Pro
            195                 200                 205

Asp Phe Gly Phe Thr Leu Leu Lys Pro Pro Asn Gln Thr Met Glu Ala
210                 215                 220

Gly Leu Asp Pro Arg Ser Leu Leu Pro Arg Thr Ala Arg Thr Leu Arg
225                 230                 235                 240

Gly Asn Arg Phe Gly Arg Pro Ile Thr Gly Val Val Ile Val Gly Met
                245                 250                 255

Ala His Gln Ile Asn Arg His Phe Ser Ala Gln Gly Thr Thr Leu Gly
                260                 265                 270

Trp Ser Thr Ala Pro Ile Gly Pro Cys Val Gly Arg Ile Asn Ser Lys
        275                 280                 285

Phe Thr Asn Thr Asn Gly Pro Ala Val Leu Ser Leu Gln Pro Leu Ser
        290                 295                 300

Asn Gly Pro Leu Tyr Pro Asn Ile Ile Asn His Tyr Pro Asp Val Ala
305                 310                 315                 320

Ala Ser Arg Ala Phe Asn Thr Ser Thr Ser Leu Gly Ala Asp Thr Thr
                325                 330                 335

Cys Gly Gly Gly Pro Met Val Val Phe Asn Asp Val Gly Asp Val Val
                340                 345                 350

Glu Thr Val Ser Tyr Gln Met Arg Phe Ile Ala Ser Gln Ala Thr Ser
            355                 360                 365

Gln Thr Pro Thr Leu Val Asp Tyr Ile Asn Ala Thr Ser Met Ala Val
        370                 375                 380

Cys Ser Tyr Gly Asn Ser Arg Gly Asp Phe Gly Ser Gly Gln Leu Asn
385                 390                 395                 400

Val Gly Val Glu Leu Thr Tyr Thr Cys Gly Thr Thr Ala Ile Asn Glu
                405                 410                 415

Lys Val Thr Thr Phe Met Asp Arg Gln Tyr Thr Phe Gly Ala Gln Gly
                420                 425                 430

Pro Asn Asn Ile Met Leu Trp Val Glu Thr Val Leu Gly Thr His Thr
            435                 440                 445

Gly Asn Asn Thr Val Tyr Ser Ser Gln Pro Asp Thr Val Ser Ala Ala
    450                 455                 460

Leu Gln Gly Gln Pro Tyr Asn Ile Pro Asp Gly Tyr Met Ala Val Trp
465                 470                 475                 480

Asn Val Asn Ala Asp Ser Ala Asp Phe Gln Ile Gly Leu Arg Arg Asp
                485                 490                 495

Gly Phe Phe Val Thr Ser Gly Ala Ile Gly Thr Arg Met Thr Ile Ser
                500                 505                 510

Glu Asp Thr Thr Phe Thr Tyr Ala Gly Met Phe Thr Leu Thr Thr Pro
            515                 520                 525

Leu Ile Gly Pro Ser Gly Met Thr Gly Arg Ser Leu His Ser Ser Gln
        530                 535                 540

Lys Gly Glu Asn Leu Tyr Phe Gln Gly His His His His His
545                 550                 555
```

```
<210> SEQ ID NO 9
<211> LENGTH: 21
<212> TYPE: DNA
<213> ORGANISM: Artificial Sequence
<220> FEATURE:
<223> OTHER INFORMATION: Reverse Primer

<400> SEQUENCE: 9
agcttccatt gtctggttag g                                              21

<210> SEQ ID NO 10
<211> LENGTH: 23
<212> TYPE: DNA
<213> ORGANISM: Artificial Sequence
<220> FEATURE:
<223> OTHER INFORMATION: Forward Primer

<400> SEQUENCE: 10
ccaaccactg atcaatccat ttg                                            23

<210> SEQ ID NO 11
<211> LENGTH: 22
<212> TYPE: DNA
<213> ORGANISM: Artificial Sequence
<220> FEATURE:
<223> OTHER INFORMATION: Reverse Primer

<400> SEQUENCE: 11
aagtctgcag agtcagcatt ta                                             22

<210> SEQ ID NO 12
<211> LENGTH: 22
<212> TYPE: DNA
<213> ORGANISM: Artificial Sequence
<220> FEATURE:
<223> OTHER INFORMATION: Forward Primer

<400> SEQUENCE: 12
ttggtgtcga actcacctat ac                                             22

<210> SEQ ID NO 13
<211> LENGTH: 22
<212> TYPE: DNA
<213> ORGANISM: Artificial Sequence
<220> FEATURE:
<223> OTHER INFORMATION: Reverse Primer

<400> SEQUENCE: 13
cgctctaaca taccaccta aa                                              22

<210> SEQ ID NO 14
<211> LENGTH: 1712
<212> TYPE: DNA
<213> ORGANISM: SAPOVIRUS

<400> SEQUENCE: 14
accgagctcg aattcatgga agccccagca cccacccgca gcgttgcttc gaaccctgaa    60
ggaacacaaa catcgaatga gtctcgccct gttcagcccg ctggaccgat gccggtagct   120
accgcacagg ctctcgaaat ggcagttgct acaggcagg taaacgatac aataccatcc   180
gttgtccgtg aaacctttag tacttatacg aatgtgacat ggacaactcg ccaacccgcc   240
ggtacgcttc tggccaggat gacacttggt cctggcctca atccctatac attgcacctc   300
tcggccatgt gggccggctg gggcggttcc ttcgagatta aggtggtaat ctcgggttcc   360
```

```
ggtctgtatg caggaaaatt gctttgtgca ttgattccac ctggcgttga tccctcagcg    420
gtagatcagc caggcgcttt cccgcatgca ttggttgatg cgcgtataac ggaaggagtt    480
acgttcacgt tgggcgatgt ccgcgcggtt gactatcacg agaccggcgc gggaggaaca    540
atagcatgcc tggcgcttta tgtttatcaa ccactgatta acccgtttga acagccttg    600
agtgcagcta tggtcacaat tgagacgaga ccgggtccag actttggttt tacattgctc    660
aagccgccaa accaaaccat ggaggccggt cttgaccccc gctcgctgtt gcctaggact    720
gcacgcacac tgagaggcaa cagattcgga cgtccgataa cgggcgtagt aatagtgggt    780
atggcccacc aaataaatag acacttctca gcacaaggaa ctacgttggg ttggtcaact    840
gcaccaatag gcccttgtgt tggcagaata acagtcgtt atacgaacag cggaggtctg    900
gcggtgctgt cgatgcaacc tctctcgaac ggacccctct atccaaatat tattaatcac    960
tacccggatg tcgccgcatc taaggcattt aacacctcaa cttctctctc tgattctact   1020
acgtgcggcg gcggtccgat ggtcatcttc aatgatgtcg gagacgtagt tgaaacagtc   1080
tcctatcaaa tgagatttat agcgtctcag gccacaagcc agactccgac tcttgtggat   1140
tacatcaacg caacgtcaat gggcctcgtc tcgtttggta atagccgtgg cgactttggc   1200
tcgggccaac ttaatgcggg cgtggaactg acatatacgt gcggtaacac tgctattaac   1260
gaaaaggtta ccacctttat ggacaggcag taccttcg cgcacaagg tcccaataat   1320
atcatgctgt gggttgagac agtgttggg acacacaccg aaataatac ggtttattcc   1380
tctcagcctg acacagtttc agccgccctc caaggtcagc cctacaatat ccctgacgga   1440
tacatggcag tttggaacgt aaacgcagat agtgcagatt ttcagatcgg ccttagacgt   1500
gatggctttt tcgttacaag cggcgcaata ggcacacgca tgaccatctc tgaagatact   1560
acattcacgt atgcaggtat cttcacgctg actacacccc tcatcggacc gtctggtatg   1620
acgggcagaa gtttgcacaa ctcgaggaag ggcgaaaact tgtactttca aggccatcac   1680
catcaccatc actaggcggc cgcttaatta at                                  1712
```

<210> SEQ ID NO 15
<211> LENGTH: 559
<212> TYPE: PRT
<213> ORGANISM: SAPOVIRUS

<400> SEQUENCE: 15

```
Met Glu Ala Pro Ala Pro Thr Arg Ser Val Ala Ser Asn Pro Glu Gly
 1               5                  10                  15

Thr Gln Thr Ser Asn Glu Ser Arg Pro Val Gln Pro Ala Gly Pro Met
            20                  25                  30

Pro Val Ala Thr Ala Gln Ala Leu Glu Met Ala Val Ala Thr Gly Gln
        35                  40                  45

Val Asn Asp Thr Ile Pro Ser Val Val Arg Glu Thr Phe Ser Thr Tyr
    50                  55                  60

Thr Asn Val Thr Trp Thr Thr Arg Gln Pro Ala Gly Thr Leu Leu Ala
65                  70                  75                  80

Arg Met Thr Leu Gly Pro Gly Leu Asn Pro Tyr Thr Leu His Leu Ser
                85                  90                  95

Ala Met Trp Ala Gly Trp Gly Gly Ser Phe Glu Ile Lys Val Val Ile
            100                 105                 110

Ser Gly Ser Gly Leu Tyr Ala Gly Lys Leu Leu Cys Ala Leu Ile Pro
        115                 120                 125

Pro Gly Val Asp Pro Ser Ala Val Asp Gln Pro Gly Ala Phe Pro His
```

-continued

```
            130                 135                 140
Ala Leu Val Asp Ala Arg Ile Thr Glu Gly Val Thr Phe Thr Leu Gly
145                 150                 155                 160
Asp Val Arg Ala Val Asp Tyr His Glu Thr Gly Ala Gly Gly Thr Ile
                    165                 170                 175
Ala Cys Leu Ala Leu Tyr Val Tyr Gln Pro Leu Ile Asn Pro Phe Glu
                180                 185                 190
Thr Ala Leu Ser Ala Ala Met Val Thr Ile Glu Thr Arg Pro Gly Pro
            195                 200                 205
Asp Phe Gly Phe Thr Leu Leu Lys Pro Pro Asn Gln Thr Met Glu Ala
        210                 215                 220
Gly Leu Asp Pro Arg Ser Leu Leu Pro Arg Thr Ala Arg Thr Leu Arg
225                 230                 235                 240
Gly Asn Arg Phe Gly Arg Pro Ile Thr Gly Val Val Ile Val Gly Met
                    245                 250                 255
Ala His Gln Ile Asn Arg His Phe Ser Ala Gln Gly Thr Thr Leu Gly
                260                 265                 270
Trp Ser Thr Ala Pro Ile Gly Pro Cys Val Gly Arg Ile Asn Ser Arg
            275                 280                 285
Tyr Thr Asn Ser Gly Gly Leu Ala Val Leu Ser Met Gln Pro Leu Ser
        290                 295                 300
Asn Gly Pro Leu Tyr Pro Asn Ile Ile Asn His Tyr Pro Asp Val Ala
305                 310                 315                 320
Ala Ser Lys Ala Phe Asn Thr Ser Thr Ser Leu Ser Asp Ser Thr Thr
                    325                 330                 335
Cys Gly Gly Gly Pro Met Val Ile Phe Asn Asp Val Gly Asp Val Val
                340                 345                 350
Glu Thr Val Ser Tyr Gln Met Arg Phe Ile Ala Ser Gln Ala Thr Ser
            355                 360                 365
Gln Thr Pro Thr Leu Val Asp Tyr Ile Asn Ala Thr Ser Met Gly Leu
        370                 375                 380
Val Ser Phe Gly Asn Ser Arg Gly Asp Phe Gly Ser Gly Gln Leu Asn
385                 390                 395                 400
Ala Gly Val Glu Leu Thr Tyr Thr Cys Gly Asn Thr Ala Ile Asn Glu
                    405                 410                 415
Lys Val Thr Thr Phe Met Asp Arg Gln Tyr Thr Phe Gly Ala Gln Gly
                420                 425                 430
Pro Asn Asn Ile Met Leu Trp Val Glu Thr Val Leu Gly Thr His Thr
            435                 440                 445
Gly Asn Asn Thr Val Tyr Ser Ser Gln Pro Asp Thr Val Ser Ala Ala
        450                 455                 460
Leu Gln Gly Gln Pro Tyr Asn Ile Pro Asp Gly Tyr Met Ala Val Trp
465                 470                 475                 480
Asn Val Asn Ala Asp Ser Ala Asp Phe Gln Ile Gly Leu Arg Arg Asp
                    485                 490                 495
Gly Phe Phe Val Thr Ser Gly Ala Ile Gly Thr Arg Met Thr Ile Ser
                500                 505                 510
Glu Asp Thr Thr Phe Thr Tyr Ala Gly Ile Phe Thr Leu Thr Thr Pro
            515                 520                 525
Leu Ile Gly Pro Ser Gly Met Thr Gly Arg Ser Leu His Asn Ser Arg
        530                 535                 540
Lys Gly Glu Asn Leu Tyr Phe Gln Gly His His His His His His
545                 550                 555
```

<210> SEQ ID NO 16
<211> LENGTH: 22
<212> TYPE: DNA
<213> ORGANISM: Artificial Sequence
<220> FEATURE:
<223> OTHER INFORMATION: Reverse Primer

<400> SEQUENCE: 16
ccttgtgctg agaagtgtct at                                              22

<210> SEQ ID NO 17
<211> LENGTH: 19
<212> TYPE: DNA
<213> ORGANISM: Artificial Sequence
<220> FEATURE:
<223> OTHER INFORMATION: Forward Primer

<400> SEQUENCE: 17
tgatccctca gcggtagat                                                  19

<210> SEQ ID NO 18
<211> LENGTH: 22
<212> TYPE: DNA
<213> ORGANISM: Artificial Sequence
<220> FEATURE:
<223> OTHER INFORMATION: Reverse Primer

<400> SEQUENCE: 18
tctcaaccca cagcatgata tt                                              22

<210> SEQ ID NO 19
<211> LENGTH: 22
<212> TYPE: DNA
<213> ORGANISM: Artificial Sequence
<220> FEATURE:
<223> OTHER INFORMATION: Forward Primer

<400> SEQUENCE: 19
gactccgact cttgtggatt ac                                              22

<210> SEQ ID NO 20
<211> LENGTH: 1712
<212> TYPE: DNA
<213> ORGANISM: SAPOVIRUS

<400> SEQUENCE: 20
accgagctcg aattcatgga ggcgcctgcg cctgcccgct ccgctgcatc caatccagaa      60
ggaacacaga cctccaatga atcgcgcccc gtgcaacctg ctggaccaat gccggtagcg     120
acagcacaag cactcgagat ggctgttgct accggtcaag taaacgacac gatccctcg     180 gttgttagag aaacattcag cacttacact aatgtcacct ggaccacccg tcaaccggcg     240
ggaacgctgc tggctcgtat gactttgggc ccaggcctca acctacac gcttcacctt     300 tcggcgatgt gggccggatg gggcggaagc ttcgagatta agtggtaat ctcaggctct     360 ggtctttatg cgggaaagct gctgtgtgcg ctcattccac cgggagtaga tccgagtgcc     420
gtggatcagc ccggtgcatt cccgcatgcc cttgtgacg caagaacgac cgagggcgtg     480
acatttacgc ttggagatgt tcgcgcagtc gattaccatg agactggagc cggtggaacc     540
atagcctgcc tcgctctcta cgtgtaccaa ccactattta tccgttcga acaacactc     600 tcggcggcta tggtcacaat cgagaccagg ccaggacccg acttcggctt tactttgctc     660

```
aaaccaccta atcaaaccat ggaggccggt cttgatccac gcagcctgct gccgcgtact    720
gctaggacgt tgcgcggaaa taggtttggc agacccataa ccgcagtcgt aattgttggc    780
atggctcatc agataaatcg ccatttctcc gctgaaggta ccactttggg atggagcacg    840
gcccctattg gaccatgtgt aggcagaata acagtcgtt atacgaataa cggaggcttg    900
gcagttttgt caatgcaacc tttgagtaat ggaccctgt atccgaatat aatcaaccac     960
tatccggacg tcgcggccag tagagccttt aatacgagta catctcttac taatgatacg   1020
acatgcggag gaggtccgat ggtcatattc aatgacgtgg gtgatgttgt cgagacggta   1080
tcgtaccaga tgcgctttat tgcatcacag gccacgtctc aaacgccaac cattgtggac   1140
tatattaatg ctacatctat gggcttggca tcttttggaa attcgcgtgg agatttcggc   1200
tccggtcaac tcaatgtggg agttgagctc acatatacct gtggtaatac tgctattaat   1260
gaaaaggtaa cgacgttcat ggatagacaa tatacattcg gagcgcaagg accaaacaat   1320
ataatgcttt gggtggaaac ggtgttgggc acacataccg gtaacaatac cgtatattct   1380
tcgcagcctg atacagtgtc tgccgcgctc caaggacaac cgtacaatat cccagatggt   1440
tatatgcgg tgtggaacgt caacgccgat tcagcagact ttcaaattgg actgaggcgt    1500
gacggcttct tcgttacgag tggcgcgatt ggaacacgta tggttatcag cgaagatact   1560
acattcacgt atgcaggtat attcaccttg acgaccccgt tgatcggtcc atctggcatg   1620
actggacgta gtctgcactc aagtcgtaag ggcgaaaact tgtactttca aggccatcac   1680
catcaccatc actaggcggc cgcttaatta at                                 1712
```

<210> SEQ ID NO 21
<211> LENGTH: 559
<212> TYPE: PRT
<213> ORGANISM: SAPOVIRUS

<400> SEQUENCE: 21

```
Met Glu Ala Pro Ala Pro Ala Arg Ser Ala Ser Asn Pro Glu Gly
 1               5                  10                  15

Thr Gln Thr Ser Asn Glu Ser Arg Pro Val Gln Pro Ala Gly Pro Met
            20                  25                  30

Pro Val Ala Thr Ala Gln Ala Leu Glu Met Ala Val Ala Thr Gly Gln
        35                  40                  45

Val Asn Asp Thr Ile Pro Ser Val Val Arg Glu Thr Phe Ser Thr Tyr
    50                  55                  60

Thr Asn Val Thr Trp Thr Thr Arg Gln Pro Ala Gly Thr Leu Leu Ala
65                  70                  75                  80

Arg Met Thr Leu Gly Pro Gly Leu Asn Pro Tyr Thr Leu His Leu Ser
                85                  90                  95

Ala Met Trp Ala Gly Trp Gly Gly Ser Phe Glu Ile Lys Val Val Ile
            100                 105                 110

Ser Gly Ser Gly Leu Tyr Ala Gly Lys Leu Leu Cys Ala Leu Ile Pro
        115                 120                 125

Pro Gly Val Asp Pro Ser Ala Val Asp Gln Pro Gly Ala Phe Pro His
    130                 135                 140

Ala Leu Val Asp Ala Arg Thr Thr Glu Gly Val Thr Phe Thr Leu Gly
145                 150                 155                 160

Asp Val Arg Ala Val Asp Tyr His Glu Thr Gly Ala Gly Gly Thr Ile
                165                 170                 175

Ala Cys Leu Ala Leu Tyr Val Tyr Gln Pro Leu Ile Asn Pro Phe Glu
            180                 185                 190
```

Thr Thr Leu Ser Ala Ala Met Val Thr Ile Glu Thr Arg Pro Gly Pro
            195                 200                 205

Asp Phe Gly Phe Thr Leu Leu Lys Pro Pro Asn Gln Thr Met Glu Ala
    210                 215                 220

Gly Leu Asp Pro Arg Ser Leu Leu Pro Arg Thr Ala Arg Thr Leu Arg
225                 230                 235                 240

Gly Asn Arg Phe Gly Arg Pro Ile Thr Ala Val Val Ile Val Gly Met
                245                 250                 255

Ala His Gln Ile Asn Arg His Phe Ser Ala Glu Gly Thr Thr Leu Gly
                260                 265                 270

Trp Ser Thr Ala Pro Ile Gly Pro Cys Val Gly Arg Ile Asn Ser Arg
            275                 280                 285

Tyr Thr Asn Asn Gly Gly Leu Ala Val Leu Ser Met Gln Pro Leu Ser
        290                 295                 300

Asn Gly Pro Leu Tyr Pro Asn Ile Ile Asn His Tyr Pro Asp Val Ala
305                 310                 315                 320

Ala Ser Arg Ala Phe Asn Thr Ser Thr Ser Leu Thr Asn Asp Thr Thr
                325                 330                 335

Cys Gly Gly Gly Pro Met Val Ile Phe Asn Asp Val Gly Asp Val Val
                340                 345                 350

Glu Thr Val Ser Tyr Gln Met Arg Phe Ile Ala Ser Gln Ala Thr Ser
            355                 360                 365

Gln Thr Pro Thr Ile Val Asp Tyr Ile Asn Ala Thr Ser Met Gly Leu
        370                 375                 380

Ala Ser Phe Gly Asn Ser Arg Gly Asp Phe Gly Ser Gly Gln Leu Asn
385                 390                 395                 400

Val Gly Val Glu Leu Thr Tyr Thr Cys Gly Asn Thr Ala Ile Asn Glu
                405                 410                 415

Lys Val Thr Thr Phe Met Asp Arg Gln Tyr Thr Phe Gly Ala Gln Gly
                420                 425                 430

Pro Asn Asn Ile Met Leu Trp Val Glu Thr Val Leu Gly Thr His Thr
            435                 440                 445

Gly Asn Asn Thr Val Tyr Ser Ser Gln Pro Asp Thr Val Ser Ala Ala
        450                 455                 460

Leu Gln Gly Gln Pro Tyr Asn Ile Pro Asp Gly Tyr Met Ala Val Trp
465                 470                 475                 480

Asn Val Asn Ala Asp Ser Ala Asp Phe Gln Ile Gly Leu Arg Arg Asp
                485                 490                 495

Gly Phe Phe Val Thr Ser Gly Ala Ile Gly Thr Arg Met Val Ile Ser
                500                 505                 510

Glu Asp Thr Thr Phe Thr Tyr Ala Gly Ile Phe Thr Leu Thr Thr Pro
            515                 520                 525

Leu Ile Gly Pro Ser Gly Met Thr Gly Arg Ser Leu His Ser Ser Arg
        530                 535                 540

Lys Gly Glu Asn Leu Tyr Phe Gln Gly His His His His His
545                 550                 555

<210> SEQ ID NO 22
<211> LENGTH: 21
<212> TYPE: DNA
<213> ORGANISM: Artificial Sequence
<220> FEATURE:
<223> OTHER INFORMATION: Reverse Primer

<400> SEQUENCE: 22

```
ggctccagtc tcatggtaat c                                              21

<210> SEQ ID NO 23
<211> LENGTH: 20
<212> TYPE: DNA
<213> ORGANISM: Artificial Sequence
<220> FEATURE:
<223> OTHER INFORMATION: Forward Primer

<400> SEQUENCE: 23
tcattccacc gggagtagat                                                20

<210> SEQ ID NO 24
<211> LENGTH: 20
<212> TYPE: DNA
<213> ORGANISM: Artificial Sequence
<220> FEATURE:
<223> OTHER INFORMATION: Reverse Primer

<400> SEQUENCE: 24
cacaatggtt ggcgtttgag                                                20

<210> SEQ ID NO 25
<211> LENGTH: 21
<212> TYPE: DNA
<213> ORGANISM: Artificial Sequence
<220> FEATURE:
<223> OTHER INFORMATION: Forward Primer

<400> SEQUENCE: 25
ggaggtccga tggtcatatt c                                              21
```